(12) United States Patent
Wang et al.

(10) Patent No.: US 7,932,490 B2
(45) Date of Patent: Apr. 26, 2011

(54) SIZE SEGREGATED AEROSOL MASS CONCENTRATION MEASUREMENT DEVICE

(75) Inventors: Xiaoliang Wang, St Paul, MN (US); Jugal Agarwal, New Brighton, MN (US); George John Chancellor, Lindstrom, MN (US); James Evenstad, Mahtomedi, MN (US)

(73) Assignee: TSI, Inc., Shoreview, MN (US)

( * ) Notice: Subject to any disclaimer, the term of this patent is extended or adjusted under 35 U.S.C. 154(b) by 460 days.

(21) Appl. No.: 12/187,827

(22) Filed: Aug. 7, 2008

(65) Prior Publication Data

US 2009/0039249 A1    Feb. 12, 2009

Related U.S. Application Data

(60) Provisional application No. 60/963,879, filed on Aug. 7, 2007, provisional application No. 60/964,008, filed on Aug. 8, 2007, provisional application No. 61/057,502, filed on May 30, 2008.

(51) Int. Cl.
*B01D 59/44* (2006.01)

(52) U.S. Cl. ...... 250/287; 250/299; 73/28.01; 73/28.04; 73/30.01; 73/335.01; 356/438; 356/439

(58) Field of Classification Search .......... 250/282, 250/287, 288, 299; 73/28.01, 28.04, 28.05, 73/29.04, 30.01, 32 R, 355.01, 863, 863.22, 73/863.03; 356/438, 439, 443
See application file for complete search history.

(56) References Cited

U.S. PATENT DOCUMENTS

| | | | |
|---|---|---|---|
| 2,732,753 A | | 1/1956 | O'Konski |
| 3,844,174 A | | 10/1974 | Chabre |
| 4,249,244 A | * | 2/1981 | Shofner et al. ............ 250/573 |
| 4,473,296 A | * | 9/1984 | Shofner et al. ............ 356/336 |
| 4,568,190 A | | 2/1986 | Carlon et al. |
| 5,089,714 A | | 2/1992 | Ludlow et al. |

(Continued)

FOREIGN PATENT DOCUMENTS

EP     0 391 256 B1    1/1994

(Continued)

OTHER PUBLICATIONS

Agarwal, Jugal K. et al. *Continuous Flow, Single-Particle-Counting Condensation Nucleus Counter*. Journal of Aerosol Science (1979) 11:343-357.

(Continued)

*Primary Examiner* — Bernard E Souw
(74) *Attorney, Agent, or Firm* — Patterson Thuente Christensen Pedersen, P.A.

(57) ABSTRACT

An apparatus and method for estimating size segregated aerosol mass concentration in real time and using a single detector. A beam of electromagnetic radiation is passed through a particle stream made of a test or field aerosol. The single detector outputs an electrical signal proportional to the electromagnetic radiation scattered thereupon. The electrical signal may be conditioned to produce an integrated signal for measuring radiation scattered from all the particles in the interrogation volume, a pulse height from an individual particle within the volume, and/or a time-of-flight measurement from the individual particle. The integrated signal can be correlated to particle mass concentration. The pulse height signal and the time-of-flight signal may be converted to infer the size of the individual particle. Attendant size distributions for the particle sizes may also be obtained. Using known or assumed particle properties, the mass concentration may be estimated from the size distribution.

29 Claims, 8 Drawing Sheets

U.S. PATENT DOCUMENTS

| | | | |
|---|---|---|---|
| 5,349,844 A | 9/1994 | Lilienfeld | |
| 5,561,515 A * | 10/1996 | Hairston et al. | 356/28 |
| 5,825,790 A | 10/1998 | Lawandy | |
| 5,932,795 A | 8/1999 | Koutrakis et al. | |
| 6,408,704 B1 | 6/2002 | Willeke | |
| 6,496,258 B1 | 12/2002 | Leipertz et al. | |
| 6,796,165 B2 | 9/2004 | Abdul-Khalek | |
| 7,057,712 B2 | 6/2006 | Beck et al. | |
| 7,111,496 B1 | 9/2006 | Lilienfeld et al. | |
| 7,476,851 B2 * | 1/2009 | Wang et al. | 250/288 |
| 7,691,636 B2 * | 4/2010 | Frazier et al. | 436/63 |
| 2002/0018204 A1 | 2/2002 | Sachweh et al. | |
| 2006/0102837 A1 * | 5/2006 | Wang et al. | 250/288 |
| 2007/0285661 A1 | 12/2007 | Saunders et al. | |
| 2008/0293146 A1 * | 11/2008 | Frazier et al. | 436/63 |
| 2009/0084979 A1 * | 4/2009 | DeWalch | 250/458.1 |
| 2009/0128810 A1 * | 5/2009 | Bates | 356/336 |
| 2009/0218481 A1 * | 9/2009 | Dewalch | 250/281 |
| 2010/0288921 A1 * | 11/2010 | Wang et al. | 250/287 |

FOREIGN PATENT DOCUMENTS

| | | | |
|---|---|---|---|
| KR | 10-1989-0702012 A | 12/1989 | |
| KR | 10-0348174 B | 2/2002 | |
| KR | 10-2005-0023339 A | 9/2005 | |

OTHER PUBLICATIONS

Abstracts of the 1996 European Aerosol Conference. *APS 3320.* Journal of Aerosol Science (1996) 27(1).

Holm, R.L. et al. *An Enhanced Time-of-Flight Spectrometer that measures Aerodynamic size plus Light-Scattering intensity*. Journal of Aerosol Science. (1996) 27(1):S11.

Vincent, James H. ed. "Summary of the Adopted Recommendations" *Particle Size-Selective Sampling for Particulate Air Contaminants*. pp. 169-178 (1999).

Armbruster, Lorenz. et al. *Photometric Determination of Respirable Dust Concentration without Elutriation of Coarse Particles*. Particle & Particle System Characterization. (1984) 96-101.

Baron, Paul, et al. *Aerosol Measurement—Principles, Techniques and Application, $2^{nd}$ ed*. pp. 419-431 (1992).

Binnig, J. *Calibration of an Optical particle Counter to provide $PM_{2.5}$ mass for well-defined particle materials*. Journal of Aerosol Science (2007) 38:325-332.

Hinds, William C. *Aerosol Technology—Properties, Behavior and Measurement of Airborne Particles* (1999) 50-55.

Sioutas, Constantinos. *Evaluation of the Measurement Performance of the Scanning Mobility Particle Sizer and Aerodynamic Particle Sizer*. Aerosol Science and Technology (1999) 30:84-92.

International Search Report, dated Dec. 12, 2008.

International Preliminary Report on Patentability, dated Feb. 18, 2010.

Hauser et al., "Smoke Particulate Sensors for OBD and high Precision Measuring", Jan. 1, 2006, 3549, copyrighted 2006 SAE Itnernational, 14 pages.

Szymanski et al., "Optical particle spectrometry-Problems and prospects", Journal of Quantitative Spectroscopy & Radiative Transfer, 2009, pp. 1-12.

Moosmüller et al., "Angular truncation errors in integrating nephelometry", Review of Scientific Instruments, vol. 74, No. 7, Jul. 2003, pp. 3492-3501.

Ruiz et al., "Effect of Gas and Kerosene Space Heaters on Indoor Air Quality: A Study in Homes of Santiago, Chile", J. Air & Waste Manage. Assoc., vol. 60, Jan. 2010, pp. 98-108.

Watson et al., "Particle Size Relationships at the Fresno Supersite", J. Air & Waste Manage. Assoc., vol. 52, Jul. 2002, pp. 822-827.

Tomasi et al., "Improved algorithm for calculations of Rayleigh-scattering optical depth in standard atmosphere", Applied Optics, vol. 44, No. 16, Jun. 1, 2005, pp. 3320-3341.

Qi et al., "Fundamental Study of a Miniaturized Disk-Type Electrostatic Aerosol Precipitator for a personal Nanoparticle Sizer", Aerosol Science and Technology, vol. 42, 2008, pp. 505-512.

Wang et al., "A Novel Optical Instrument for Estimating Size Segregated Aerosol Mass Concentration in Real Time", Aerosol Science and Technology, vol. 43, 2009, pp. 939-950.

TSI Incorporated, Health and Safety Brochure, Mass Concentration Comparison Between the DustTrak™ DRX Aerosol Monitor and TEOM, May 2008, pp. 1-6.

TSI Incorporated, Particle Instruments Brochure, "Model 3321 Aerodynamic Particle Sizer Spectrometer", 2004, pp. 1-8.

Sreenath et al., "Performance of a New Hybrid Aerosol Photometer", Presentation, 2008, TSI Incorporated pp. 1-19.

California Measurements, Inc.—Air Particle Analyzers and Samplers Brochure, Apr. 27, 2010, pp. 1-3, http://www.californiameasurements.com/html/product.html.

Wang, TSI, Incorporated, Development and Characterization of the TSI DustTrak DRX Aerosol Monitor, prior to Aug. 2007, 1 page.

Mulholland, "Dust and Aerosol Measurement Feasibility Test (DAFT)" Flyer, TSI, Incorporated presentation, PTL Seminar, prior to Aug. 2007, 1 page.

TSI, Incorporated, "PSD 3603 Particle Size Distribution Analyzer", 2002, 2 pages.

Application and File History for U.S. Appl. No. 12/705,398, filed Feb. 12, 2010. Inventors: Xiaoliang Wang et al. at www.uspto.gov.

* cited by examiner

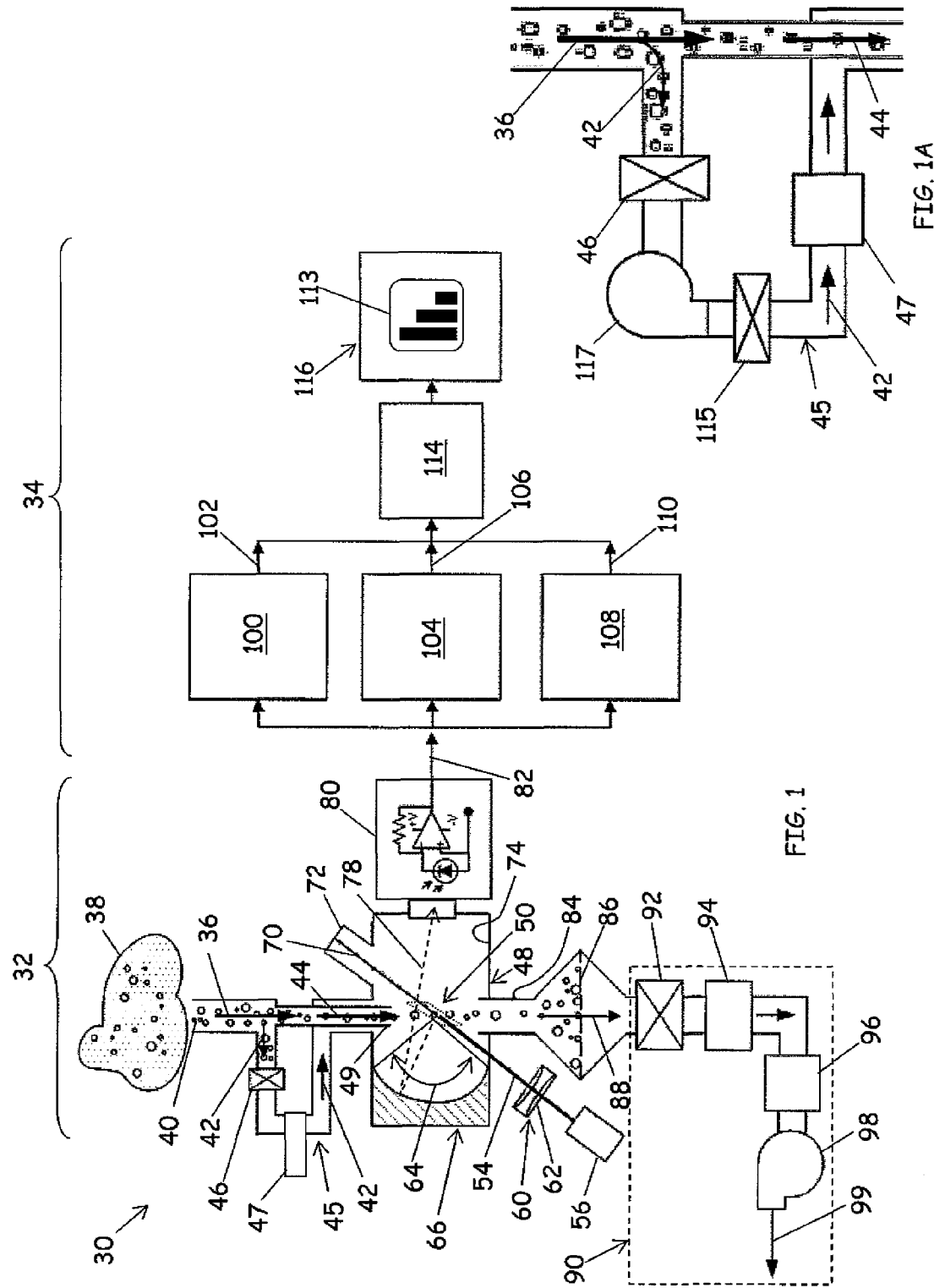

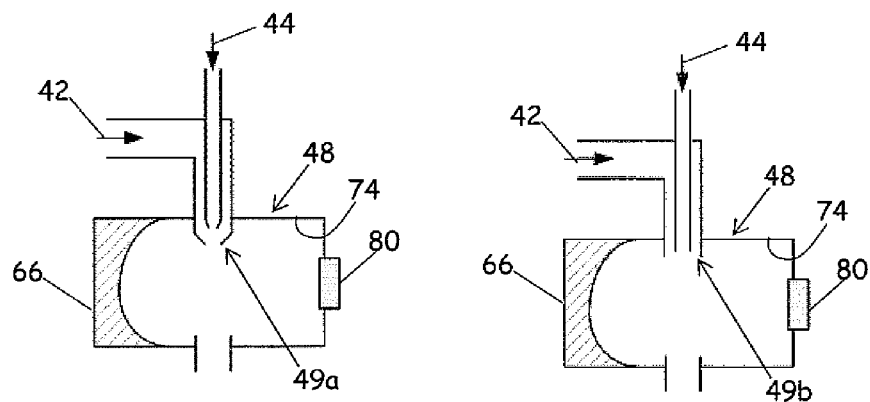
Fig. 2A
Fig. 2B
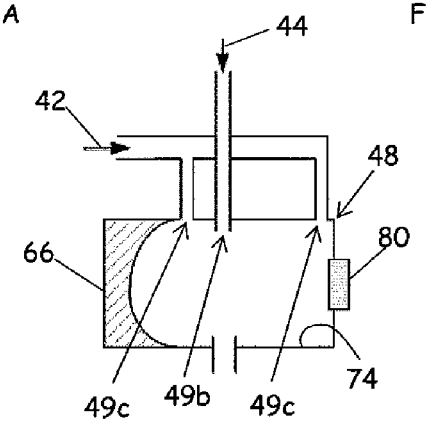
Fig. 2C
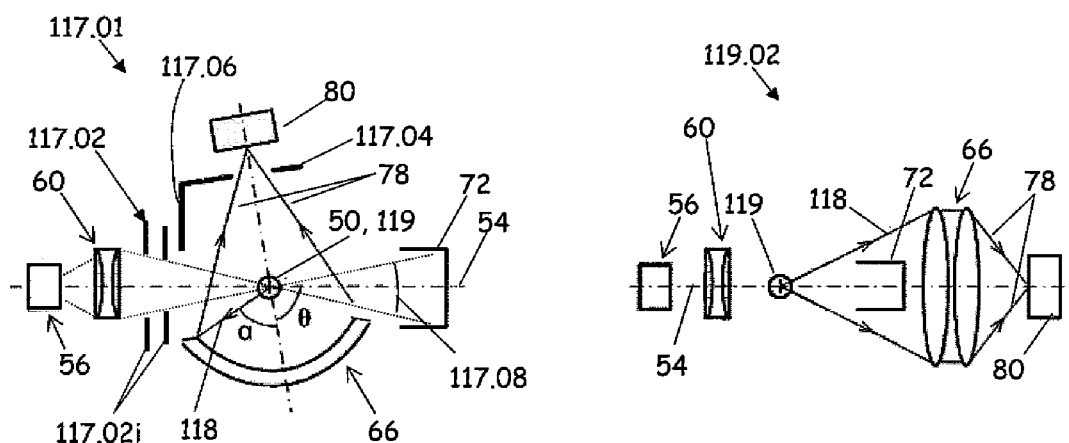
Fig. 3A
Fig. 3B

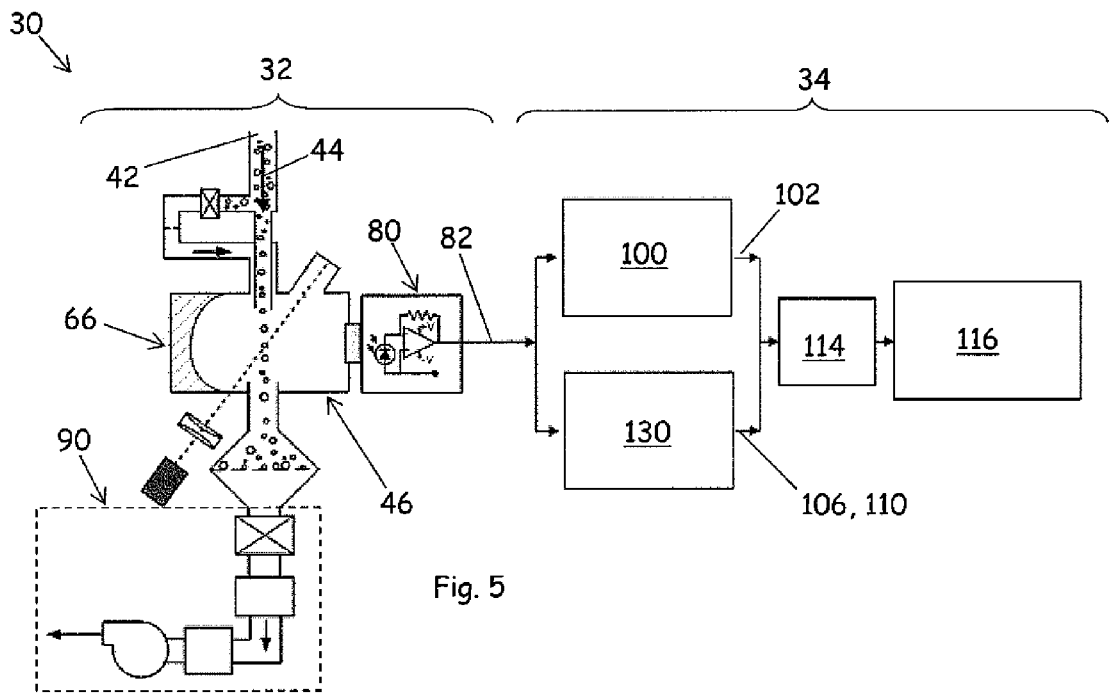
Fig. 5
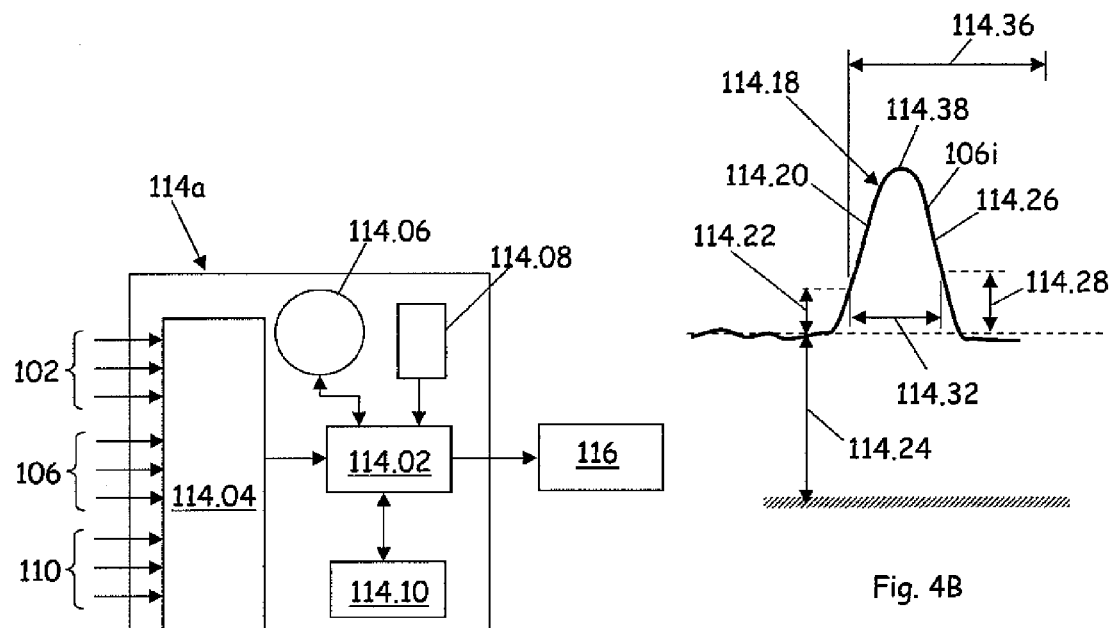
Fig. 4A
Fig. 4B

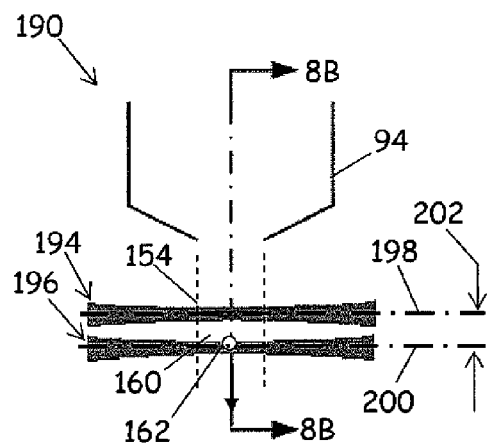
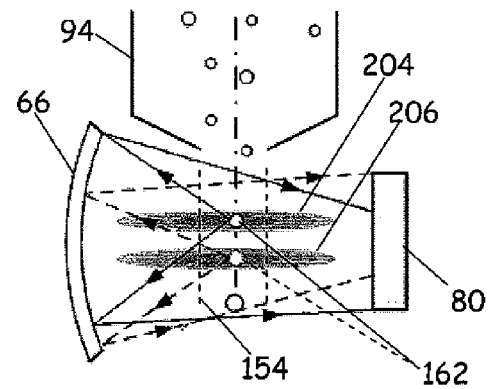
Fig. 8A
Fig. 8B
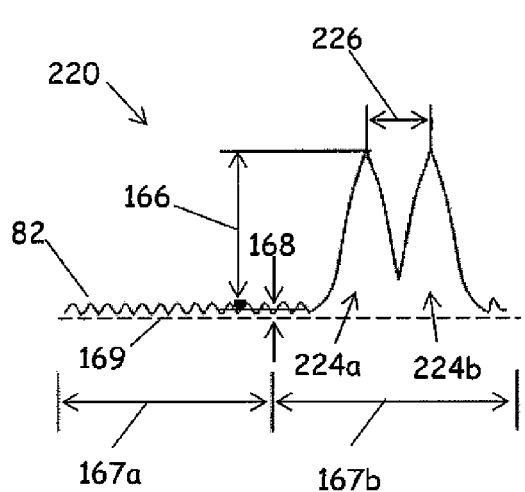
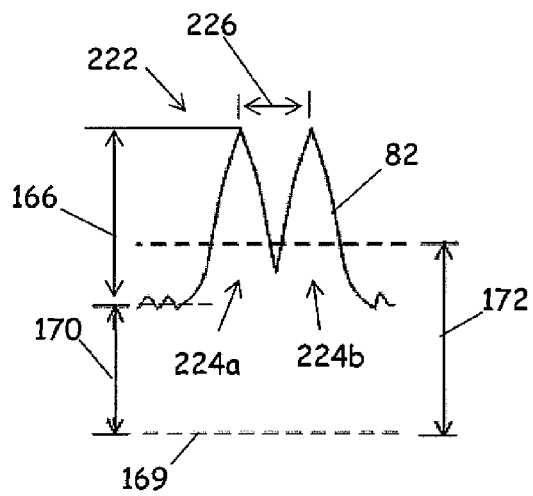
Fig. 8C
Fig. 8D

SIZE SEGREGATED AEROSOL MASS CONCENTRATION MEASUREMENT DEVICE

RELATED APPLICATIONS

The present application claims the benefit of U.S. Provisional Application No. 60/963,879, filed Aug. 7, 2007, U.S. Provisional Application No. 60/964,008, filed Aug. 8, 2007, and U.S. Provisional Application No. 61/057,502, filed May 30, 2008, the disclosures of which are hereby incorporated by reference.

FIELD OF THE INVENTION

The present disclosure relates generally to the detection of particles, and more specifically to the measurement of dust particle concentrations and size distributions.

BACKGROUND OF THE INVENTION

Aerosols commonly found in the environment are generated both by nature and human activity. They influence human lives in many ways. Aerosols in the atmosphere can absorb and/or scatter light and change visibility as well as the earth energy balance. Atmospheric aerosols also serve as condensation sites for cloud formation, thus playing an important role in the climate. When inhaled, aerosol particles can deposit on the respiratory track and cause adverse health effects.

Industry and government have recognized the importance of measuring and monitoring aerosol concentrations in the environment or workplace so that proper measure can be taken to reduce potential health risks. Pertinent monitoring applications include but are not limited to industrial/occupational hygiene surveys, outdoor ambient/site perimeter monitoring for dust control operations, and engine emission studies. Some industrial processes require knowledge of the particulates in the environment, including environments having a sparse population of particles (e.g., semiconductor manufacturing) as well as environments having an extensive presence of particle populations (e.g., dry powder manufacturing processes).

In 1987, the United States Environmental Protection Agency (EPA) revised the National Ambient Air Quality Standards (NAAQS) and started to use mass of particles with aerodynamic diameters less than approximately 10 µm (hereinafter "the PM10") as the particulate matter (PM) pollution index. The PM10 is an index of the PM that can enter the thorax and cause or exacerbate lower respiratory tract diseases, such as chronic bronchitis, asthma, pneumonia, lung cancer, and emphysema. It was later determined that PM concentrations in the air, as indexed by the mass of particles with aerodynamic diameters less than approximately 2.5 µm ("PM2.5") was more closely associated with the annual mortality rates than with the coarser PM10. In 1997, in its next revision of the NAAQS, the EPA promulgated regulations on PM2.5. Recently, there has been extensive discussion on the health effects of particles smaller than 1 µm (i.e. "PM1"). As of the filing date of this application, PM1 has not been adopted as a federal standard.

The American Conference of Governmental Industrial Hygienists (ACGIH) has also established sampling conventions of respirable, thoracic and inhalable aerosols, defined as particles having aerodynamic diameters of less than 4 µm, 10 µm, and 100 µm respectively. Inhalable particles are those capable of entering through the human nose and/or mouth during breathing. Thoracic particles are the inhaled particles that may penetrate to the lung below the larynx. Respirable particles are the inhaled particles that may penetrate to the alveolar region of the lung. A discussion of the various sampling conventions are found at *National Primary and Secondary Ambient Air Quality Standards,* 40 Code of US Federal Regulation, Chapter 1, Part 50 (1997) and Vincent, J. H., Particle Size-Selective Sampling for Particulate Air Contaminants Cincinnati, ACGIH (1999), both of which are hereby incorporated by reference except for explicit definitions contained therein.

While the aforementioned standards and conventions are based on the aerodynamic diameters of particles, it is understood that size segregated mass concentration groupings (e.g., PM1, PM2.5, PM10, respirable, thoracic and inhalable) may be based on the optical particle diameters instead of the aerodynamic diameters for purposes of the instant application. That is, PM2.5 (for example) may approximate particles having an aerodynamic diameter of less than approximately 2.5 µm or particles having an optical diameter of less than approximately 2.5-µm.

Presently, the federal reference method (FRM), which utilizes filter samplers, is implemented to determine compliance with mass based air quality standards. The filter samplers typically include a size selective inlet to remove particles larger than a specified size and a filter media to collect particles, which is weighed to obtain the particulate mass. The disadvantage of the filter method is that a long sampling time (normally hours) may be required to collect enough mass on the filter. Also, the results are not available until the samples are analyzed in the laboratory. Thus, FRM devices are not suitable for real time measurements.

Particle mass measurements can be achieved in real time using a photometer if the aerosol is primarily a fine aerosol (approximately between 0.1- and 4-µm). The photometer is a device that produces an electrical signal that varies with the intensity of scattered light received from a particle or an ensemble of particles in the interrogation volume region. The photometric signal can be approximately correlated to particle mass. The photometer may also be sensitive to a wide dynamic range of particle concentration. For example, the TSI Model 8520 DUSTTRAK photometer measures a particle mass concentration range of 0.001- to 100-mg/m$^3$ over the particle size range of 0.1- to 10-µm.

Some disadvantages of various photometers are: (1) only the total mass is measured (no particle size segregated mass information is provided); (2) the photometric signal is dependent on particle properties such as size, shape and refractive index, thus requiring different calibration factors for different aerosols; (3) photometers are typically more sensitive to particles having diameters close to the wavelength of the light source, with a precipitous drop off in signal per unit mass for particles outside of this size range; and (4) photometers can underestimate particulate mass if the sampled aerosol contains particles larger than 4 µm.

One instrument that measures particle size dependent number concentrations in real time is the optical particle counter (OPC), such as disclosed in U.S. Pat. No. 2,732,753, the disclosure of which is hereby incorporated by reference herein other than express definitions of terms specifically defined therein. In an OPC, particles pass through an interrogation volume that is illuminated by a light beam. The light scattered by each particle is collected on to a detector to generate an electrical pulse. From the pulse height (i.e. the intensity of the scattered radiation) one can infer the particle size based on prior calibration. Because the size inferred from the OPC depends on the particle optical properties, the inferred parameter is often referred to as the "optical equivalent particle size." By assuming aerosol properties such as density, shape and refractive index, the size distribution can be converted to mass distribution, such as described by Binnig, J., J. Meyer, et al. "Calibration of an optical particle counter to provide PM2.5 mass for well-defined particle materials," *Journal of Aerosol Science* 38(3): 325-332 (2007), which is hereby incorporated by reference herein other than express definitions of terms specifically defined therein.

Some advantages of the OPC are: (1) particles may be counted with high accuracy for low particle concentrations; (2) favorable signal to noise ratios for particle sizes greater than 1 µm; and (3) low cost. However, the inferred particle optical size may not be the same as the actual or geometric particle size because the determination depends on the particle shape and refractive index assumptions. Additional errors may arise when converting the particle size distribution to a mass concentration if the particle density is incorrectly assumed. Furthermore, OPCs typically underestimate particle concentration when multiple particles are present in the interrogation volume region (a condition often referred to as "coincidence error"). Accordingly, OPCs are typically only used in relatively clean environments. An example is the TSI Model 8220 OPC, which counts 95% of particles at a number concentration of approximately 200 particles/$cm^3$ or mass concentrations less than 1-mg/$m^3$. The counting efficiency of the Model 8220 drops quickly as concentration increases above these limits.

Another instrument that measures particle size distribution in real time is an Aerodynamic Particle Sizer (APS), such as described in U.S. Pat. No. 5,561,515 to Hairston et al., assigned to the assignee of the instant application, the disclosure of which is hereby incorporated by reference herein other than express definitions of terms specifically defined therein. When particles of different sizes are accelerated through an accelerating nozzle, larger particles may tend to be accelerated to a lesser extent through the interrogation volume(s) than smaller particle because the larger particles may possess a greater inertia to overcome. The APS exploits this principle by accelerating particles through a nozzle to obtain size dependent particle velocities, which are typically measured by measuring the time-of-flight of the particles through the sensing zone. Unlike the OPC measurement, the APS measurement is independent of the particle refractive index. Also, while converting the particle size distribution to mass distribution, the APS is less sensitive to the particle density parameter than the OPC measurement. Good agreement between the mass concentrations calculated from APS spectra and from direct mass measurements has been demonstrated in the size range of 0.5- to 10-µm. See Sioutas, C. (1999). "Evaluation of the Measurement Performance of the Scanning Mobility Particle Sizer and Aerodynamic Particle Sizer." *Aerosol Science and Technology* 30(1): 84-92.

A disadvantage of the APS is that only particle populations of relatively low concentration (e.g., on the order of 1000-particle/$cm^3$ and lower) can be measured due to coincidence error. For example, the TSI Model 3321 APS accurately measures aerodynamic particle size distributions in the 0.5- to 20-µm range, (with 5% coincidence error) up to approximately 1000-particles/$cm^3$. The APS resolution decreases with the particle size. Also, all commercially available instruments are relatively expensive.

Commercially, the TSI Model 3321 APS provides the combination of an APS and an OPC devices in a single unit. The Model 3321 determines particle size utilizing APS techniques. The OPC device provides the user with additional information that may be utilized, for example, to create a time-of-flight and a light scattering correlation. As with other existing APS and OPC devices, the Model 3321 is still limited to applications in relatively low particle concentrations.

The TSI Model 3321 APS utilizes the aerodynamic particle diameters of the detected particles to calculate the mass concentration of the aerosol. Other commercially available particle counters, such as the Grimm Model #180 Ambient Dust Monitor, manufactured by Grimm Aerosol Technik GmbH & Co. KG of Ainring, Germany, utilize the optical particle diameters of detected particles to calculate the mass concentration. Effectively, the mass of each detected particle is calculated assuming the particle to be spherical and of known density. Calibration factors may also be applied to account for correct the non-spherical shape and differing density of the particles. Inherent limitations to this approach are that the mass calculation is not based on detection of the smaller diameter particles (less than approximately 0.3-µm optical or aerodynamic diameter) that go undetected by the APS or OPC detector. Also, this approach is limited to low concentration applications.

In summary, the filter sampling provides first principle mass measurement, but has poor time resolution and it does not provide particle size information. Obtaining size segregated mass concentration measurements may require the procurement and maintenance of multiple instruments. The photometer measures a wide particle concentration range, but it does not provide particle size information and may be relatively insensitive to particles having diameters greater than approximately 4-µm. The OPC or APS measures the size dependent concentrations, but are typically functional only at relatively low particle concentrations.

An instrument that can provide size segregated particle mass concentrations information in real time and over a wide range of mass concentrations that mitigates the shortcomings of existing approaches would be welcome.

SUMMARY OF THE INVENTION

Various embodiments of the invention include a hybrid apparatus and/or method for determining the particle size distribution and mass distributions in the particle size range of interest (collectively referred to herein as size segregated aerosol mass concentration) and in real time. The disclosed device may include as many as three signal conditioning circuits in communication with a single detector. The signal conditioning circuits may provide a simultaneous and real time indication of the mass concentration, optical particle size distribution and aerodynamic particle size distribution of the interrogated particle stream. Size segregated mass concentration can be measured over a wider concentration range than those existing instruments. Various aspects of the invention can also provide more accurate mass concentration measurement than existing instruments, while providing additional information about particle sizes.

The measurement may be performed on particles suspended in a medium such as a liquid, a gas or some combination thereof. When the medium is a gas, the product is known as an aerosol. The gas may be air, nitrogen, argon, helium, carbon dioxide or any other gas or gas mixtures. Particles can be solid, liquid or a combination of both. Certain embodiments of the invention may be configured as a single or unitary instrument.

A challenge in utilizing a common detector for photometric detection in combination with OPC and/or APS detection is stray or background radiation, especially when the photometric technique is to measure very low mass concentrations (e.g., on the order of 1-µg/$m^3$). The detector in a photometric device measures background or stray radiation as well as the targeted radiation scattered by the particles in the viewing volume. Moreover, the level of background radiation is susceptible to change. Factors such as temperature change and particle deposition on surfaces inside the measuring chamber may cause the background radiation to vary over time. The detector cannot distinguish between the change in the background radiation level and changes in the targeted radiation. At low particle concentrations, the intensity of the targeted radiation is typically quite low, and the background radiation may comprise a substantial portion of the total radiation received by the detector. Hence, for accurate low aerosol concentration measurements, it is desirous to mitigate at least the changes to the background radiation.

Such concerns are typically not addressed in conventional photometric devices. Available photometric devices utilize relatively large diameter light beams so as to define a larger interrogation volume and provide a more representative sampling of the aerosol stream. The larger diameter light beam typically provides a lower watt density within the interrogation volume for a given light beam power level, and may also utilize longer focal length optics for narrow convergence/divergence angles adjacent the interrogation volume. Moreover, the narrow convergence/divergence angle of the light beam exposes less surface area to radiation than a wide angle. Accordingly, stray radiation scattered from the interrogation volume that finds its way back to the detector is of minimal concern for standard photometric devices.

The OPC and APS devices, on the other hand, utilize highly focused light beams that define small interrogation volumes. The smaller interrogation volume limits the occurrence of coincidence; the concentrated light beam provides a scattered signal that is strong enough to produce a pulse having a pulse height, pulse width and/or dual peak pulse separation with sufficient resolution to perform the sizing task. Accordingly, stray radiation scattered from the interrogation volume is of substantially greater watt density than in standard photometric detection devices. Also, to achieve a highly focused light beam at the interrogation volume, optics having shorter focal lengths are typically employed, with attendant wide convergence/divergence angles, thus bathing larger surface areas (e.g., optics, light traps) that can scatter with radiation than with narrower angles. Hence, the stray radiation in conventional OPC and APS devices that finds its way back to the detector, while being of little consequence to an OPC or APS measurement, can cause significant bias to the photometric signal.

To address the problem of stray radiation bias of the photometric signal, various embodiments of the invention include ways to limit the propagation of stray radiation to the detector, such as light beam apertures, detector apertures and strategically placed baffles to limit the background radiation.

Some embodiments of the invention are capable of providing size segregated mass concentrations (e.g., PM10, PM2.5 and PM1, or inhalable, thoracic and respirable fractions) using a single detection device and over a wide concentration range in real time. At low particle concentrations (e.g., when the coincidence error is less than about 5%), where the integrated signal may be insensitive, the size distribution may be measured using techniques akin to an OPC and/or an APS device and a mass concentration inferred therefrom.

At higher concentrations, where the integrated signal analysis is feasible, the integrated photometric signal may strongly correlate with the fine particle mass concentration (e.g., PM2.5 and respirable fractions) and weakly correlate with coarse particle mass fractions (e.g., PM10 and thoracic). When this occurs, modified single particle counting techniques may be implemented that count only particles greater than a certain size (e.g., 1-μm) and to ignore smaller particles because of the attendant high coincidence error. The real time mass concentration of each size segregated mass fraction can be obtained by math operations applied to the integrated signal and to the pulse signals generated because of the larger single particles.

Structurally, certain embodiments of the invention implement an incident beam of electromagnetic radiation (hereinafter "light beam") that defines a first interrogation volume through which a suspended particle stream passes. Other embodiments utilize a dual beam configuration that further comprises a second incident light beam defining a second interrogation volume located downstream of the first interrogation volume. In either embodiment, a portion of the light that is scattered from the interrogation volume(s) by the particles may be sensed by a single detector.

In some embodiments, the detector generates an electrical signal proportional to the scattered light received from particles. The electrical signal may be processed by a plurality of signal conditioning circuits, including: (1) an integrated or total signal (photometric signal) proportional to the intensity of incident light that is scattered by the particle or ensemble of particles in the interrogation volume and intercepted by the detector; (2) a pulse height signal derived from scattered light originating from individual particles; and (3) a time-of-flight signal providing a direct or indirect measurement of the particle velocity through the interrogation volume region. The integrated signal may comprise a biased or time-averaged signal that can be correlated to particle mass concentration, especially if the particles within the interrogation volume are made of primarily fine or respirable particles. The pulse height signal may be indicative of the particle optical equivalent size. With respect to the time-of-flight signal circuit, the particle time-of-flight is proportional to the width of the pulse from which the particle aerodynamic diameter may be inferred. For the dual beam configuration, the time-of-flight is directly measured as the time lag between characteristics of successive signal pulses (e.g., the signal peaks) to calculate the particle aerodynamic diameter.

From the pulse height signal and the time-of-flight signal, the optical and aerodynamic particle size distributions may be inferred. Given the properties of the particles (e.g., shape, refractive index, density), the mass concentration may be inferred from the particle size distribution. At low particle concentrations (i.e. when the integrated signal is low), both the size and the mass concentrations can be inferred from either optical or aerodynamic size distribution techniques, or both. Particle distributions of naturally occurring aerosols are known to have greater populations at smaller diameters. Accordingly, as the particle concentrations increase, light pulses originating from the more populous small particles may no longer be distinguishable from each other due to coincidence. However, the population of the larger particles (e.g., diameters greater than 1-μm) may be sufficiently sparse for size and mass distribution determination. The mass concentration can be obtained by performing mathematical operations on the single particle counting signals and on the integrated signal. In this way, the size segregated mass fractions such as PM1, PM2.5, PM10, inhalable, thoracic and respirable may be obtained from a single instrument or detector.

In one embodiment, an instrument for measuring size segregated mass concentration of an aerosol is disclosed, comprising an electromagnetic radiation source operatively coupled with beam shaping optics for generation of a beam of electromagnetic radiation. An inlet nozzle for passage of an aerosol flow stream therethrough may also be included, the aerosol flow stream containing particles and intersecting the beam of electromagnetic radiation to define an interrogation volume so that the particles scatter the electromagnetic radiation from the interrogation volume. A radiation collector may be included for collection of a portion of the electromagnetic radiation scattered from the interrogation volume, as well as a detector for detection of the portion of the electromagnetic radiation collected by the radiation collector. In this embodiment, a plurality of signal conditioners including an integrated signal conditioner and at least one of a pulse height signal conditioner and a time-of-flight signal conditioner may be operatively coupled to the detector, each generating a respective output. A digital processor may be operatively coupled with the plurality of signal conditioners for conversion of each of the respective outputs to a mass concentration and to at least one of an optical particle size and an aerodynamic particle size.

Various embodiments that employ the time-of-flight signal conditioner may further include additional beam shaping optics for generation of a second beam of electromagnetic radiation, the second beam of electromagnetic radiation intersecting the aerosol flow stream to define a second interrogation volume, the particles scattering the electromagnetic radiation from the second interrogation volume, the radiation collector being arranged for collection of a portion of the electromagnetic radiation scattered from the second interrogation volume. Additional beam shaping optics comprising a beam splitter and the second beam of electromagnetic radiation may be sourced by the electromagnetic radiation source. The system may further comprise a gravimetric filter positioned downstream of the interrogation volume.

In another embodiment of the invention, a device for determining size segregated aerosol mass concentration comprises a detector operatively coupled to an integrated signal conditioner and at least one of a pulse height signal conditioner and a time-of-flight signal conditioner, the integrated signal conditioner for generation of an integrated output, the pulse height signal conditioner for generation of a pulse height output, the time-of-flight signal conditioner for generation of a time-of-flight output. A signal processor is included in this embodiment, configured to receive the integrated signal output and at least one of the pulse height output and the time-of-flight signal output, the signal processor including a microprocessor and a storage device. The storage device may include instructions executable by the microprocessor, the instructions including resolving an integrated mass concentration from the integrated output and resolving a particle size from at least one of the pulse height output and the time-of-flight output. The instructions may also include using the particle size to calculate a size resolved mass concentration and inferring a size segregated mass concentration from the integrated mass concentration and the size resolved mass concentration, the size segregated mass concentration having a plurality of size fraction bands. The size fraction bands may include one or more of a PM1, a PM2.5, a respirable fraction and a PM10. The detector may be operatively coupled to the pulse height signal conditioner and the time-of-flight signal conditioner, wherein the instructions executable by the microprocessor may further include: determining particle size for particles within a first size range using the pulse height output; determining particle size for particles within a second size range using the time-of-flight output, the second size range having an average size that is greater than an average size of the first size range; and determining a size resolved mass concentration from the first and second size ranges.

Other embodiments of the invention comprise a method for determining size segregated aerosol mass concentration, the method including: providing a detector operatively coupled with an integrated signal conditioner and with a pulse height signal conditioner, the detector configured to receive electromagnetic radiation scattered from an interrogation volume; causing particles to flow through the interrogation volume and scatter electromagnetic radiation onto the detector to generate an electrical signal from the detector; generating an integrated output from the electrical signal with the integrated signal conditioner, the integrated output being proportional to a mass of particles flowing through the interrogation volume during a predetermined time interval; generating a plurality of pulse height outputs from the electrical signal with the pulse height signal conditioner, each of the pulse height outputs corresponding to a particle passing through the interrogation volume and corresponding to an optical particle size greater than a predetermined value; and determining a size segregated mass concentration from the from the integrated output and the plurality of pulse height outputs. The method may further comprise inferring a plurality of optical particle sizes from the plurality of pulse height outputs and the integrated output, one for each of the plurality of pulse height outputs, calculating a plurality of optical particle masses from the plurality of optical particle sizes, one optical particle mass for each of the plurality of optical particle sizes, inferring a mass concentration from the integrated output, and determining a size segregated mass concentration from the mass concentration and the plurality of optical particle masses. The method may also further comprise: generating a plurality of time-of-flight outputs from the electrical signal with the time-of-flight signal conditioner, each of the time-of-flight outputs corresponding to a particle passing through the interrogation volume and corresponding to an aerodynamic particle size greater than a predetermined value; inferring a plurality of aerodynamic particle sizes from the plurality of time-of-flight outputs and the integrated output, one for each of the plurality of time-of-flight outputs; calculating a plurality of aerodynamic particle masses from the plurality of aerodynamic particle sizes, one aerodynamic particle mass for each of the plurality of aerodynamic particle sizes; inferring a mass concentration from the integrated output; and determining a size segregated mass concentration from the from the mass concentration and the plurality of aerodynamic particle masses. The detector provided in this method may further comprise providing the detector operatively coupled with a time-of-flight signal conditioner.

In another embodiment, a method for determining size segregated aerosol mass concentration includes: providing a detector operatively coupled with an integrated signal conditioner and with a time-of-flight signal conditioner, the detector configured to receive electromagnetic radiation scattered from an interrogation volume; causing particles to flow through the interrogation volume and scatter electromagnetic radiation onto the detector to generate an electrical signal from the detector; generating an integrated output from the electrical signal with the integrated signal conditioner, the integrated output value being proportional to a mass of particles flowing through the interrogation volume during a predetermined time interval; generating a plurality of time-of-flight outputs from the electrical signal with the time-of-flight signal conditioner, each of the time-of-flight outputs corresponding to a particle passing through the interrogation volume and corresponding to an aerodynamic particle size greater than a predetermined value; and determining a size segregated mass concentration from the from the integrated output and the plurality time-of-flight outputs. This method may also comprise inferring a mass concentration from the integrated output; inferring a plurality of aerodynamic particle sizes from the plurality of time-of-flight outputs and the integrated output, one aerodynamic particle size for each of the plurality of time of flight outputs; calculating a plurality of aerodynamic particle masses from the plurality of aerodynamic particle sizes, one aerodynamic particle mass for each of the plurality of aerodynamic particle sizes; and determining a size segregated mass concentration from the from the mass concentration and the plurality of aerodynamic particle masses. This method may further include generating a plurality of pulse height outputs from the electrical signal with the pulse height signal conditioner, each of the pulse height outputs corresponding to a particle passing through the interrogation volume and corresponding to an optical particle size greater than a predetermined value; inferring a plurality of optical particle sizes from the plurality of pulse height outputs and the integrated output, one for each of the plurality of pulse height outputs; calculating a plurality of optical particle masses from the plurality of optical particle sizes, one optical particle mass for each of the plurality of optical particle sizes; inferring a mass concentration from the integrated output; and determining a size segregated mass concentration from the from the mass concentration and the plurality of optical particle masses.

In other embodiments, a method for determining size segregated aerosol mass concentration, comprises providing a detector operatively coupled a pulse height signal conditioner and a time-of-flight signal conditioner, the pulse height signal conditioner for generation of a pulse height output, the time-of-flight signal conditioner for generation of a time-of-flight output; causing the detector to receive electromagnetic radiation scattered from a particle; resolving an optical particle size value from the pulse height output; resolving an aerodynamic particle size from the time-of-flight output; establishing a size of the particle to be the optical particle size if one of the optical particle size and the aerodynamic particle size is less than a predetermined value; and establishing a size of the particle to be the aerodynamic particle size if one of the optical particle size and the aerodynamic particle size is greater than a predetermined value.

Various methods may utilize the aerodynamic particle size to characterize a first size range of particles and the optical particle size is utilized to characterize second size range of particles, the first size range having a first average value, the second size range having a second average value, the first average value being greater than the second average value.

A representative and non-limiting sensitive size range for the various embodiments of the invention is from 0.1- to 20-μm. A non-limiting dynamic range of particle mass concentration is 0.0001- to 400-mg/m³. Certain embodiments may include an optional filter installed downstream of the optical chamber to collect particles for direct mass measurement. Other appurtenances include devices for controlling parameters such as light power and flow rate for more reliable instrument operation, accuracy and ease of use.

BRIEF DESCRIPTION OF THE DRAWINGS

FIG. 1 is a schematic diagram depicting a size segregated mass concentration measurement system in an embodiment of the invention.

FIG. 1A is a schematic diagram depicting a bypass loop for independent control of the aerosol and sheath flow rates in an embodiment of the invention.

FIG. 2A is a schematic depicting an accelerating inlet nozzle with sheath flow for use in FIG. 1 in an embodiment of the invention.

FIG. 2B is a schematic depicting a straight inlet nozzle with sheath flow for use in FIG. 1 in an embodiment of the invention.

FIG. 2C is a schematic diagram depicting a straight inlet nozzle with curtain/purge flow for use in FIG. 1 in an embodiment of the invention.

FIG. 3A is a plan view of an optical configuration with collection optics arranged at an arbitary angle θ relative to the incident beam in an embodiment of the invention.

FIG. 3B is a plan view of an optical configuration with collection optics that are substantially co-linear with the incident beam in an embodiment of the invention.

FIG. 4A is a partial schematic diagram of the digital processor of FIG. 4.

FIG. 4B depicts a pulsed signal and various components of a pulse height analysis executed by the digital processor of FIG. 4A in an embodiment of the invention.

FIG. 5 is a schematic diagram of a size segregated mass concentration measurement system in an embodiment of the invention.

FIG. 8A depicts a dual beam source for use in various embodiments of the invention.

FIG. 8B is a sectional view of the dual beam arrangement of FIG. 8A.

FIGS. 8C and 8D depict output signal pulses generated by the dual beam configuration of FIGS. 8A and 8B at different particle concentrations in an embodiment of the invention.

DETAILED DESCRIPTION OF THE DRAWINGS

Figure 4:
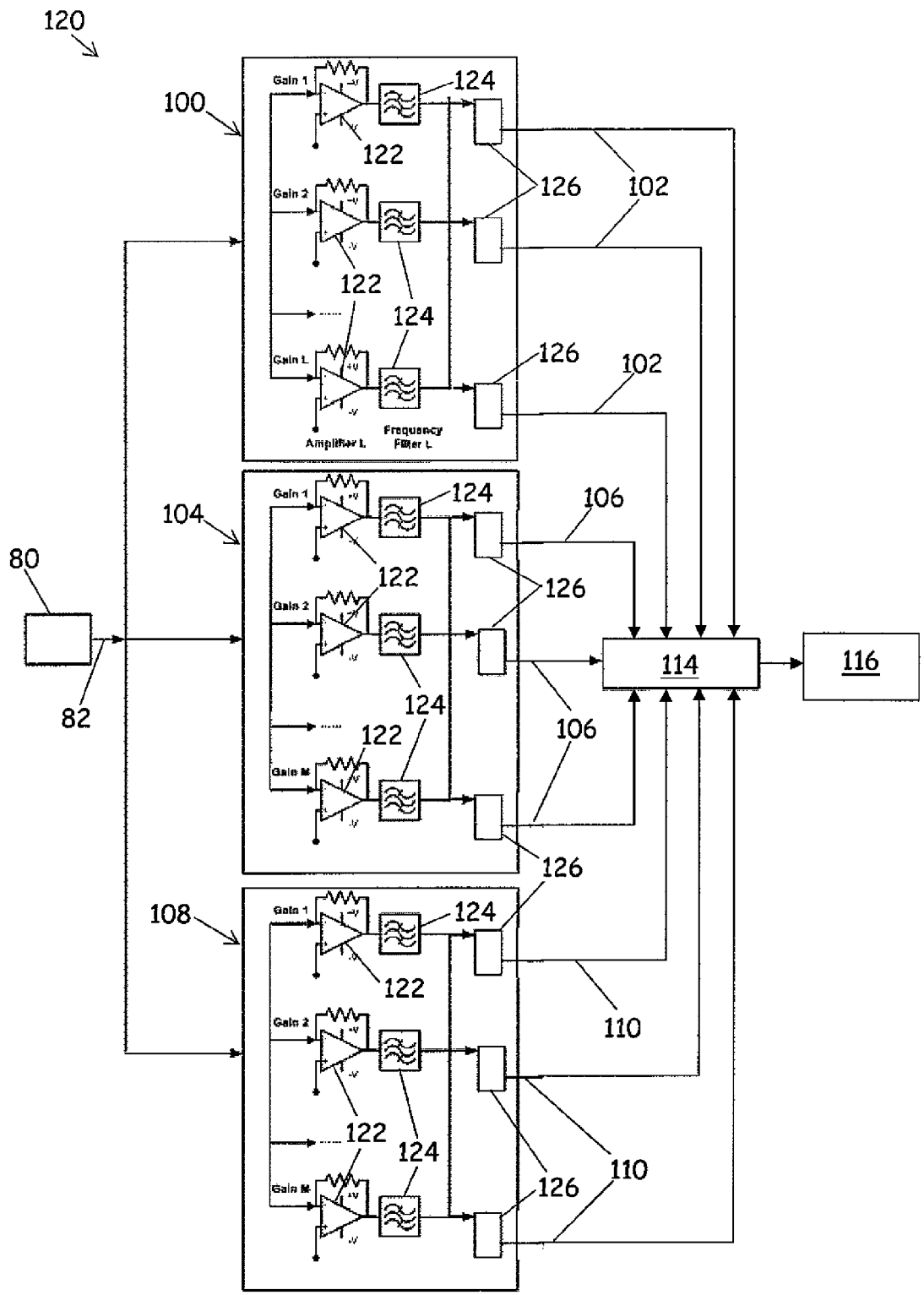
FIG. 4 is a partial schematic diagram depicting the three circuits of FIG. 1 in more detail in an embodiment of the invention.

Referring to FIG. 1, a size segregated mass concentration measurement system 30 comprising an aerosol measurement section 32 and a signal acquisition and processing section (SAPS) 34 is schematically depicted in an embodiment of the invention. An incoming flow stream 36 may be drawn from an aerosol cloud 38 through an inlet 40 of the aerosol measurement section 32. The incoming flow stream 36 may be split into a sheath flow stream 42 and an aerosol flow stream 44. The sheath flow stream 42 may be diverted to a sheath flow conditioning loop 45 that may include a filtration device 46 and a flow measuring device 47. The aerosol flow stream 44 may be passed through an inlet nozzle 49 to an optics chamber 48 that includes a viewing or interrogation volume 50. The interrogation volume 50 may be defined by the intersection of a light beam 54 and the aerosol flow stream 44. The light beam 54 may be sourced from an electromagnetic radiation source 56 such as a diode laser, a LED or a lamp (broadband or line emitting).

The size segregated mass concentration measurement system 30 may further comprise beam shaping optics 60 that may include a lens 62 such as a cylindrical lens. The shaping optics 60 may additionally or alternatively comprise reflective components such as mirrors, or fiber optic components (not depicted). A portion of the light scattered from particles over a solid angle 64 may be subtended by a light collection system or radiation collector 66 (e.g., a spherical mirror, aspheric condenser lenses, or other electromagnetic radiation collection devices available to the artisan) within the optics chamber 48. An unscattered portion 70 of the light beam 54 may be captured by a light trap 72. Inner surfaces 74 of the optics chamber 48 may be coated with a black or high absorptivity coating such as an anodized coating. Collected light 78 gathered by the radiation collector 66 may be transferred to a detector 80 such as a photodiode or a photomultiplier tube. The detector 80 may produce an electrical signal 82 proportional to the convolution of the incident electromagnetic radiation and the spectral sensitivity of the detector 80.

In some embodiments, the aerosol flow stream 44 exits the optics chamber 48 through an outlet nozzle 84 and may be passed through a gravimetric filter 86, thereby producing a pre-filtered aerosol flow stream 88. The aerosol flow streams 44 may be drawn through the optics chamber 48 by a pumping system 90 that includes a protection filter 92, a flowmeter 94, a flow pulsation damping chamber 96 and a pump or blower 98 that is ducted to an exhaust 99. Numerous kinds of pumps or blowers may be utilized, including but not limited to a diaphragm pump, a rotary vane pump, a piston pump, a roots pump, a linear pump or a regenerative blower.

In one embodiment, the SAPS 34 may condition the electrical signal 82 to define three different signal circuits: an integrated or total signal conditioner circuit 100 for generating integrated outputs 102 proportional to watt density of the collected light 78 gathered by the radiation collector 66 and incident on the detector 80; a pulse height conditioner circuit 104 for detecting scattered light originating from individual particles as they pass through the interrogation volume 50 and generating pulse height outputs 106 in accordance therewith; and a time-of-flight conditioner circuit 108 providing time-of-flight outputs 110 that provides a direct or indirect measurement of the velocities of certain particles as they pass through the interrogation volume 50. The outputs 102, 106 and 110 may be routed to a digital processor 114 for analysis and subsequent conversion into a size segregated mass concentration distribution 113. The result can be output to a device 116, such as a display, a storage device, analog output or a computer.

Functionally, beam shaping optics 60 may be utilized to configure the shape of the light beam 54 and interrogation volume 50 to possess certain characteristics, such as overall width and height, as well as intensity profile. The light trap 72 mitigates or prevents biasing of the electrical signal 82 that may be caused by the unscattered portion 70 of the light beam 54 gathered by the radiation collector 66 after multiple scattering within the optics chamber 48. When utilized, the high absorptivity coating on the inner surfaces 74 of the optics chamber 48 may further reduce the propagation of stray light.

In operation, the integrated signal conditioner circuit 100 provides integrated signals akin to that produced by a photometric device (i.e. proportional to the light flux scattered from all the particles in the interrogation volume region). The pulse height output 106 and time-of-flight output 110 are akin to the outputs of OPC and APS devices, respectively.

Particles can be collected on the gravimetric filter 86 and can be weighed to measure mass directly. This direct mass measurement can be used to create the calibration relationship between the electrical signal 82 and the mass of the collected particles (see discussion attendant FIG. 9). Particles on the gravimetric filter 86 can also be analyzed to study their chemical compositions. The protection filter 92 may remove particles remaining in the air stream 88 upstream of the flowmeter 94 and pump or blower 98 for protection against particle contamination, especially in configurations where there is no gravimetric filter in place. The pump or blower 98 may be used to drive the flow through the whole system. The flow pulsation damping chamber 96 is an optional device that may reduce the pulsation of flow in the system.

The filtration device 46 of the sheath flow conditioning loop 45 removes particulates from the sheath flow stream 42 to provide a substantially clean flow of gas that shrouds or sheaths the aerosol flow 44. The cleansed sheath flow 42 helps contain particulates within the core of the aerosol flow 44 as it passes through the optics chamber 48, thereby mitigating against particulate contamination of the optics chamber 48 and appurtenances therein. The flow measuring device 47, when utilized, can provide an indication of the flow rate of the sheath flow stream 42 which can be subtracted from the total flow rate of the incoming flow stream 36 provided by the flowmeter 94 to determine the flow rate of the aerosol flow stream 44.

Referring to FIG. 1A, an alternative arrangement for the sheath flow conditioning loop 45 is depicted in an embodiment of the invention that includes a sheath flow pump 117. A second filter 115 may also be included.

In operation, the sheath flow pump 117 enables independent control of the flow rate of the sheath flow stream 42. The filtration device 46 serves not only to cleanse the sheath flow stream 42, but also to protect and prevent contamination of the sheath flow pump 117 from the removed particles. A function of the second filter 115 is to capture particles that may be generated by the sheath flow pump 117 and prevent them from fouling the flow measuring device 47 and to maintain the purity of the sheath flow stream 42 after exiting the sheath flow pump 117.

Referring to FIGS. 2A through 2C, various configurations for the inlet nozzle 49 and delivery of the sheath flow stream 42 are depicted in embodiments of the invention. A converging inlet nozzle 49a is depicted in FIG. 2A for accelerating both the aerosol flow stream 44 and the sheath flow stream 42, while FIGS. 23 and 2C depict a straight nozzle 49b. The sheath flow stream 42 of FIGS. 2A and 2B are depicted as being concentric or collinear with the aerosol flow stream 44 as the flows 42 and 44 enter the optics chamber. In the embodiment depicted in FIG. 2C, the sheath flow stream 42 is directed through a plurality of perimeter inlets 49c (e.g., nozzles or slots) to flow over or close to the inner surfaces 74 of the optics chamber 48, thereby producing a curtain or purge flow.

In operation, the converging inlet nozzle 49a may accelerate different sized particles to different velocities so that aerodynamic diameters can be inferred from the velocities or time-of-flight outputs 110. (See FIGS. 11 and 12 and attendant discussions regarding time-of-flight measurements and calibrations.) Thus, an accelerating nozzle is particularly well suited for time-of-fight measurements. Configurations other than a convergent diameter may be utilized that produce an acceleration, such as a blockage within the throat that directs through an annulus having a reduced cross-sectional area.

Functionally, the sheath flow streams 42 of FIGS. 2A through 2C may reduce particle deposition inside the optics chamber 48 and help keep the optics clean for longer periods and/or between maintenance intervals. The configurations depicted in FIGS. 2A and 2B may also help contain particles within the aerosol flow stream 44, thus better defining the aerosol flow stream 44 as it passes through the interrogation volume 50. The approach depicted in FIG. 2C may reduce the dead flow volumes or stagnation flow regions within the optics chamber.

Referring to FIG. 3A, an off-axis optical configuration 117.01 is depicted in an embodiment of the invention. The off-axis optical configuration 117.01 may include an aperture train 117.02 comprising a plurality of aperture plates 117.02$i$ centered about the light beam 54, a detector aperture plate 117.04 centered in front of the detector 80, and a baffle 117.06. The baffle may be integral with (as depicted) or separate from the detector aperture plate 117.04.

The radiation collector 66 may be arranged to subtend or collect light that is scattered from the light beam 54 at a preferred angle. Scattered radiation 118 that is scattered from a particle or particles 119 within the interrogation volume 50 has generally different intensities at different scattering angles. That is, the intensity of the scattered radiation is generally dependent on the angle at which the radiation is scattered. A "scattering angle" is defined as the angle between the forward direction of an incident beam of radiation and the scattered light beam.

An inclination angle $\theta$ is defined between the incident light and the center axis of the collecting optics. A portion of the scattered radiation 118 may be collected over the scattering angles of $\theta \pm \alpha°$ of by the radiation collector 66, where $\alpha$ is the half angle of the solid angle subtended by the light collecting optics. The collected light 78 may be transferred to the detector 80.

Functionally, the apertures 117.02, 117.04 and baffle 117.06 configuration of FIG. 3A also portrays structure for mitigating background or stray radiation. There are at least three primary sources for background radiation: (1) scatter from the surfaces of the beam shaping optics 60; (2) reflected radiation from the tip of the aerosol inlet nozzle 49; and (3) radiation escaping the light trap 72. Generally, the contribution to the background radiation from these sources can be reduced by implementing an aperture train 117.02 comprising a plurality of aperture plates 117.02$i$ centered between the beam shaping optics 60 and the interrogation volume 50. The edge of a given aperture plate 117.02$i$ becomes a new source of background radiation which is obstructed by a subsequent aperture plate. The process of using several aperture plates 117.02$i$ is only practical if there is enough space between the beam shaping optics 60 and the aerosol inlet nozzle 49. Accordingly, the background radiation may be best mitigated or controlled using beam shaping optics 60 of relatively long focal length in combination with the aperture train 117.02. As an additional measure, a detector aperture plate 117.04 may be placed in front of the detector 80.

However, implementation of the OPC or APS techniques normally requires the light beam 54 be tightly focused into a small interrogation volume 50 to achieve adequate watt density so that the radiation scattered by the aerosol flow stream 44 will generate an adequate signal-to-noise ratio. Such focusing of the light beam 54 is generally accomplished by tailoring the beam shaping optics 60 for a short focal length. Compared to long focal length light beams, short focal length light beams not only limit the number of aperture plates 117.02$i$ that can be utilized, but also creates a larger converging/diverging angle 117.08 in the light beam on both sides of the interrogation volume 50. Thus, more surface areas are exposed to the direct light beam 54, thus increasing the potential for unwanted scatter of radiation that contributes to the background radiation.

Implementation of the aperture train 117.02 and detector aperture plate 117.04 was found to be only partially effective in certain low concentration applications. It was discovered that some radiation exiting the aperture train 117.02 would impinge directly on the interior edge of the detector aperture plate 117.04 and be reflected directly onto the detector. In certain configurations, this direct line radiation scattered off the interior edge defining the aperture of the detector aperture plate 117.04 was found to the largest single contributor to background radiation.

The baffle 117.06, properly positioned, was found to effectively block the direct line radiation between the aperture train 117.02 and the detector aperture plate 117.04 while not affecting the radiation scattered from the interrogation volume 50. The position of the baffle 117.04 was also substantially removed from the aerosol flow stream 44 so as not to disturb the flow of the aerosol stream 44.

Referring to FIG. 3B, a co-axial optical configuration 119.02 is depicted in an embodiment of the invention, where the axis of the radiation collector 66 is concentric or collinear with the light beam 54, and the radiation collector 66 is located behind the light trap 72.

Referring to FIG. 4, a circuit schematic 120 of the three conditioner circuits 100, 104 and 108 are depicted in greater detail. The signal 82 from the detector may be simultaneously analyzed by the three conditioner circuits 100, 104 and 108. Each circuit may comprise a number of signal amplifiers 122, frequency filters 124 and analog-to-digital (A/D) converters 126. For each circuit, only data from one of the gain stages having the best accuracy and resolution is used for the subsequent processing at each specific time. The circuits 100, 104 and 108 may differ in the number and selection of the components (e.g., the amplification factor of signal amplifiers 122, the filtering frequency of the frequency filters 124, and the digitization rate and resolution of the A/D converters 126) to achieve the objectives of the respective circuits. The gains are set to obtain a preferred resolution and accuracy. The filters are selected to remove noise while retaining desired signal and adequate response. The A/D converters are selected for adequate sampling speed and resolution. For example, the integrated signal conditioner circuit 100 may include four to six amplifiers having gains ranging from 1 to 5000, a low pass filter of 0.1- to 10-Hz, and a 0.5- to 1.0-MHz A/D converters with 10- to 16-bits resolution. The pulse height and time-of-flight conditioner circuits 104 and 108 may have two to four amplifiers with gains ranging from $\frac{1}{50}$ to 40, a low pass filter having a frequency in the 0.5- to 1.0-MHz range, and a 10- to 20-MHz A/D converter with 10- to 12-bit resolution. The ranges provided above are illustrative only and is not to be construed as limiting the invention.

The digital signal processor 114 may be configured to analyze the outputs 102, 106 and 110 from the three conditioner circuits 100, 104 and 108 concurrently and in real time. The digital processor 114 may include, but is not limited to, a Field Programmable Gate Array (FPGA), a microprocessor, a digital signal processor, an application-specific integrated circuit (ASIC), or some combination thereof.

Referring to FIG. 4A, an example embodiment of a signal processor 114$a$ is depicted in an embodiment of the invention.

In this embodiment, the signal processor 114a comprises a microprocessor 114.02 operatively coupled with a FPGA 114.04, a dead time clock 114.06, a read-only memory device 114.08 (e.g., a ROM or PROM), a digital memory device 114.10 (e.g., RAM), and the output device 116. The FPGA 114.04 may be configured to accept the digital signals from the various outputs 102, 106 and 110.

The integrated outputs 102 from the integrated signal conditioner circuit 100 may be monitored continuously. The values of the integrated outputs 102 may be determined by the FPGA 114.04. Depending on the value of the integrated outputs 102, it may be that only one of the integrated outputs 102 is useful. For example, for a mid-range output level, the amplifiers 122 configured for higher gains may be saturated, whereas the channels 122 configured for lower gains have signals too small (high signal-to-noise ratio) for analysis. Accordingly, the FPGA 114.04 may be programmed to select the integrated output 102 having the highest value that is not saturated and pass that value on to the microprocessor 114.02. The value may then be transferred to the microprocessor 114.02 and stored in an appropriate memory bin in the digital storage device 114.10 or device 116.

Referring to FIG. 4B, a method of processing a given pulse height output 106i employed by the signal processor 114a is depicted in an embodiment of the invention. To analyze the signals from the pulse height conditioner circuit 104, the FPGA 114.04 may be configured to continuously monitor the pulse height outputs 106 from the pulse height conditioner circuit 104 section of signal in real time. The pulse height outputs 106 may be subject to several criteria before the signal processor 114 registers the presence of a particle. For example, one criterion may be that a rising edge 114.20 of the given pulse height output 106i exceeds a predetermined threshold 114.22. The predetermined threshold 114.22 may be taken relative to a given baseline signal 114.24 taken prior to the occurrence of the rising edge 114.20 crossing the predetermined threshold 114.22.

When the given pulse height output 106i meets the rising edge criterion, the dead-time clock 114.06 may be triggered. Another criterion may be that a falling edge 114.26 of the pulse height output 106i also falls below a second threshold 114.28. A time lapse 114.32 between the rising edge 114.20 crossing the threshold 114.22 and the falling edge 114.26 crossing the second threshold 114.28 may also be monitored to meet another criterion that the time lapse 114.32 be within a predetermined time differential 114.36. The digital processor 114a may be programmed to monitor the incoming data streams from the outputs 106 for the various criteria. When at least one of the outputs 106 meet the various criteria, the signal processor 114a may be programmed to select the output 106 from the amplifier 122 of the pulse height conditioner circuit 104 having the lowest gain that still satisfies the criteria. The signal processor 114a may then register that a particle has been detected, and pass the information such as a peak value 114.38 from the selected output 106 to the microprocessor 114.02 for further processing. After the FPGA 114.04 determines whether or not the pulse represents a particle, the elapsed time from the dead-time clock may be recorded and reset, and the FPGA directed to resume the monitoring function.

The analysis of the time-of-flight outputs 110 may be very similar to the analysis of the pulse height outputs 106. A primary difference is that a time interval 114.40 between two events such as the threshold crossing of FIG. 4B or a peak-to-peak time interval (not depicted) rather than the peak value 114.38 is used as the useful signal.

The microprocessor may be programmed to poll the FPGA 114.04 at a given rate, for example, once per second. The microprocessor 114.02 may use predetermined calibration factors and data analysis algorithms to calculate the size segregated mass concentration, as explained in more detail below.

Some embodiments may include or use only the integrated signal conditioner circuit 100 in combination with either the pulse height conditioner circuit 104 or the time-of-flight conditioner circuit 108. In some applications, these alternative configurations may still achieve the goal of measuring size segregated mass concentration over a wide concentration range in real time.

Referring to FIG. 5, a combined pulse height and time-of-flight conditioner 130 is depicted in an embodiment of the invention. The combined pulse height and time-of-flight conditioner 130 may be particularly viable where the specification of the components for pulse height conditioner circuit 104 and the time-of-flight conditioner circuit 108 are of substantial similarity so that the conditioned pulse height and time-of-flight outputs 106 and 110 would be substantially similar. The combined pulse height and time-of-flight conditioner 130 provides further compactness, economy and simplicity of construction and maintenance.

Figure 6:
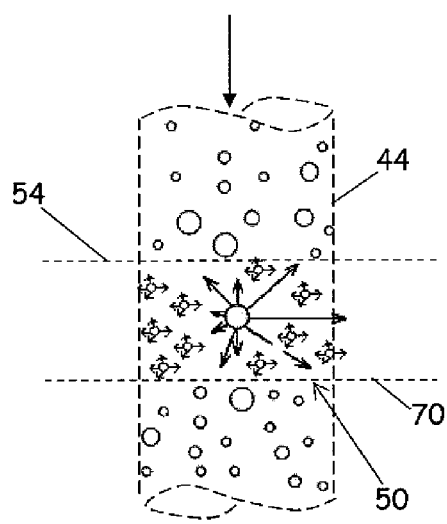
FIG. 6 depicts a beam of radiation being scattered by an aerosol flow stream in an embodiment of the invention.

Referring to FIG. 6, the scattering of light beam 54 in the control volume 50 of FIG. 1 is depicted. For optically thin media (optical thickness less than approximately 0.1), it can be assumed that the radiation incident on the detector 80 has been scattered only once by the irradiated particles; that is, the contribution to the electrical signal 82 originating from multiple scattering (radiation scattered from one particle and subsequently reflected off a second particle) can be assumed negligible.

Figure 7A:
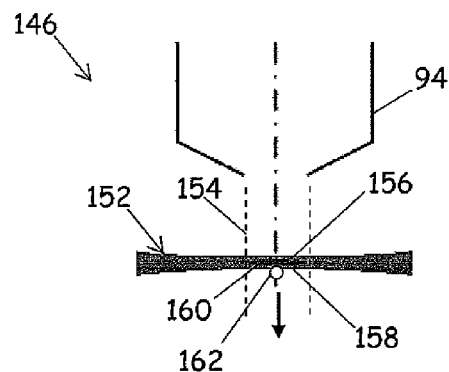
FIG. 7A depicts a single light beam source for use in the device of FIG. 1.
Figure 7B:
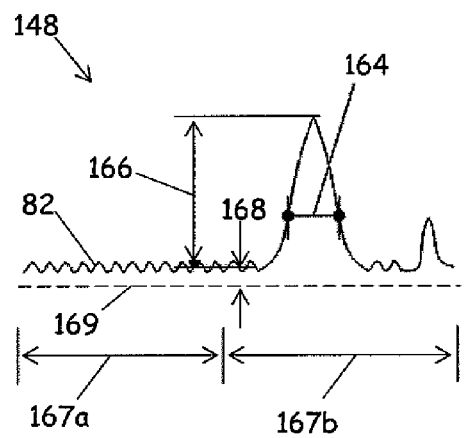
FIG. 7B depicts an output signal from the single beam configuration device of FIG. 7A at low particle concentrations in an embodiment of the invention.
Figure 7C:
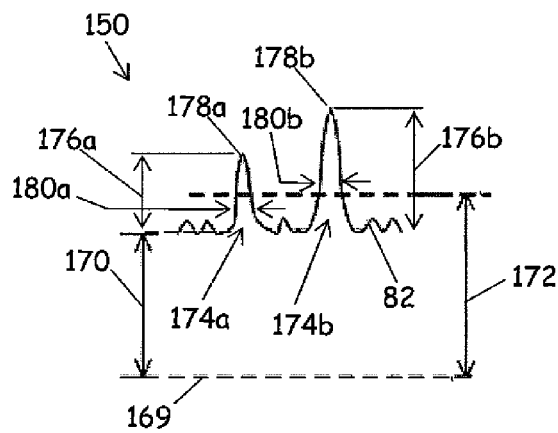
FIG. 7C depicts an output signal from the single beam configuration device of FIG. 7A at high particle concentrations in an embodiment of the invention.

Referring to FIG. 7A through 7C, a single beam configuration 146 for producing signals such as the time-of-flight signals 148 (FIG. 7B) and 150 (FIG. 7C) is depicted for use in an embodiment of the invention. The single beam configuration 146 comprises a single light beam 152 that intersects an aerosol flow stream 154. The single light beam may be characterized as having a local upstream boundary 156 and a local downstream boundary 158 of the light beam 152. An interrogation volume 160 is defined as the portion of the aerosol flow stream 154 that is bounded by the upstream and downstream boundaries 156 and 158 of the light beam 152.

The local upstream and downstream boundaries 156 and 158 may be defined as the location within the aerosol flow stream 154 where the intensity of light beam 152 is a certain fraction or percentage of the peak intensity of the light beam 152. A common industry practice is to define the beam boundary as the contour where the ratio of the local intensity to the maximum intensity of the beam is $1/e^2$, where e is Euler's number (equal to approximately 2.72). Still another way to define the beam is by the full width at half the maximum intensity (FW technique). For various embodiments of the invention, definition of the beam boundaries or volume may be inconsequential because the pulse width may be determined by predefined thresholds. Beam shaping optics (e.g., numerical reference 60 of FIG. 1) may shape the light beam 152 so that the boundaries 156 and 158 are substantially parallel within the aerosol flow stream 154.

In the single beam configuration 146, the time-of-flight is inferred from a pulse width measurement, as depicted in FIG. 7B. If the boundaries 156 and 158 are substantially parallel to each other, the time required for a given particle 162 traversing the single light beam 152 at a given trajectory will be the same regardless of where in the aerosol flow stream 154 the particle 160 traverses the single light beam 152.

An analysis of example time-of-flight signals 148 and 150 is depicted in FIGS. 7B and 7C, respectively, for single beam configurations such as depicted in FIGS. 1 and 7A. The time-of-flight signal 148 may be representative of a signal such as the electrical signal 82 generated by the detector 80 by virtue of the detector 80 being irradiated with the collected light 78 scattered from the particle 162. The time-of-flight signal 148 is representative a signal that would be generated by a low or sparse concentration of particles in the aerosol flow stream 44. A pulse width 164 may be defined as the time difference between the leading edge and the trailing edge of the detected pulse at an arbitrary percentage or fraction (e.g., 50%) of a pulse height 166.

When there is no particle present in the detection region, such as depicted by time interval 167a, the electrical signal 82 output by the detector 80 may be characterized by a baseline signal 168 that is greater than a true ground level 169, arising from background noise such as stray light and electronic noise. When the particle concentration is low, the integrated outputs 102 may be representative of the baseline signal 168, except for the integration of pulses generated by individual particles, such as depicted in time interval 167b. Also at low concentrations the optical equivalent and aerodynamic particle diameters can be obtained independently from the pulse height and width measured with the same circuit, as discussed previously attendant FIG. 5.

The analysis of the time-of-flight signal 148 assumes a low concentration of particulates in the aerosol flow stream 44. An "intermediate concentration" particle stream exists when the integrated signal is still low but the occurrence of coincidence becomes too frequent to ignore (e.g., a coincidence error in the approximate range of 5% to 20%). In this regime, the single particle counting may be extended to higher concentrations utilizing "live time" coincidence correction. When the digital signal processor 114 is analyzing the collected light 78 scattered by the particle 162, active monitoring of the interrogation volume 160 ceases. A new particle in the viewing volume during this unmonitored or "dead time" period may not be registered. Therefore, only the "live time', which is the difference of the total sampling time and the dead time, should be used to calculate particle concentration. Hering et al., "A Laminar-Flow, Water-Based Condensation Particle Counter (WCPC)," *Aerosol Science and Technology* 39(7): 659-672 (2005), which is hereby incorporated by reference herein other than express definitions of terms specifically defined therein, describes live time correction in further detail.

The time-of-flight signal 150 (FIG. 7C) is representative a signal that may be generated by a high concentration of particles in the aerosol flow stream 44. A "high concentration" particle stream exists when the integrated outputs 102 includes a detectable bias or offset because of the continuous presence of particles in the interrogation volume 50. In this regime, the pulse height outputs 106, time-of-flight output 110 and the integrated outputs 102 may be measured simultaneously.

The analog output of the time-of-flight signal 150, such as would be seen in the electrical signal 82 output by the detector 80, may be characterized as having a nominal offset level or value 170, a time-averaged integrated level 172, and as having distinguishable pulses such as represented by pulses 174a and 174b. The time-averaged integrated level 172 may be considered an analog equivalent of the integrated outputs 102. In FIG. 7C, the integrated level 172 appears elevated relative to the nominal offset level 170 because the integrated level 172 may be inclusive of the integration or "area" under pulses 174a and 174b in addition to the nominal offset level 170.

Pulses 174a and 174b may further be characterized as having pulse heights 176a and 176b with local maxima values 178a and 178b, respectively, and pulse widths 180a and 180b, respectively. The pulse heights 176a, 176b may be defined as the difference between the local maxima values 178a, 178b and the nominal offset value 170.

The integrated outputs 102 may be established over an integration period that is long relative to the pulse duration. That is, the integration period for the integrated signal 102 may be orders of magnitude greater than the pulse width of the signal generated by a typical particle (e.g., 174a). For example, the pulse width may be on the order of 5-μsec, whereas the integration period may be on the order of 500- to 1000-μsec. Accordingly, the integrated signal 102 is relatively steady with respect to the short pulses of individual larger particles (microsecond time frame), but is still sensitive to changes in the baseline signal due to general increases/decreases in the aerosol concentration (millisecond time frame).

In operation, the integrated conditioner circuit 100 may resolve the time-averaged integrated level 172 and output the integrated outputs 102 to the digital processor 114 for determination of the mass concentration, utilizing a calibration. (See FIG. 9 and attendant discussion for an example of a mass concentration calibration curve.)

The pulse heights 176a, 176b and pulse widths 180a, 180b may be resolved and utilized by the conditioner circuits 104 and/or 108 and analyzed to infer the optical sizes and the aerodynamic sizes, respectively, of the corresponding particles that traversed the single light beam 152. The analysis may comprise use of calibration curves to infer the optical and/or aerodynamic sizes, such as by look-up tables or curve fit functions that are programmed into the digital processor 114. (See FIGS. 10 and 11 and attendant discussion for examples of particle sizing calibration curves.)

The digital processor 114 may also be configured to infer the mass concentrations within a plurality of size fraction bands (e.g., PM1, PM2.5 and PM10, respirable, thoracic) and the size segregated mass concentration distribution 113 determined therefrom. For example, because aerodynamic sizing is more suitable for larger particle diameters, the particle mass fractions for large particles may be more accurately determined from the aerodynamic particle size (e.g., 2.5- to 10-μm, or "PM2.5-10"), and the particle mass fractions for particles of smaller diameter (e.g., 1 to 2.5 μm, or "PM1-2.5") may be more accurately determined from the optical particle size determination.

Referring to FIGS. 5A and 8B, a dual beam configuration 190 for determination of particle time-of-flight is depicted in an embodiment of the invention. The dual beam configuration 190 includes a first light beam 194 and a second light beam 196 that traverse the aerosol flow stream 154. Each of the first and second light beams 194 and 196 may be characterized by a respective central propagation axis 198 and 200. The central propagation axes 198 and 200 may be substantially parallel to each other with a separation distance 202 defined therebetween. The first and second light beams 194 and 196 can be formed in various ways, including origination from a single source that is split using an optical device, such as a polarization beam splitter (not depicted). An example of such a splitter is found in the TSI Model 3321 APS, manufactured by the assignee of the current application. The light beams 194 and 196 may be further characterized as having perimeters 204 and 206 (FIG. 8B). Also, the beams are depicted as being clearly separated, but in practice may overlap, so long as the central propagation axes 198 and 200 are separated.

With the dual beam configuration 190, the time-of-flight may be determined by measuring the time difference between two successive signal pulses (see FIG. 8C and attendant discussion below). This type of measurement may be referred to as a "pulse-to-pulse" measurement. Because the time between the two successive peaks will be the same regardless of the intensity of the light beams 194 and 196 across the trajectory of the particle 162, the perimeters 204 and 206 may define any cross-sectional shape (e.g., elliptical or circular), so long as each of the light beams 194 and 196 subtend the aerosol flow stream 154.

Light scattered from the particle 162 as it passes through the first and second light beams 194 and 196 may be gathered by the collector 66 and transferred to the detector 80 (FIG. 5B). Alternatively, the light scattered by the respective light beams 194 and 196 may be detected by separate detectors (not depicted), each arranged to view only one of the light beams 194 and 196. The time-of-flight may be determined a number of ways, including utilization of a hardware circuit (e.g., triggering a clock on the rising edge of the first pulse and reading the clock upon detection of the rising edge of the second pulse) or by digital analysis of the pulse shapes as they become available in real time or in a post-test analysis. The pulse widths of the first and/or second signal pulses may also be utilized to augment the time-of-flight determination.

Referring to FIGS. 8C and 8D, an analysis of pulse-to-pulse signals 220 and 222, each generated by the dual beam configuration 190, is depicted in an embodiment of the invention. The pulse-to-pulse signal 220 may be representative of the analog electrical signal 82 made with a low concentration aerosol, and may have characteristics similar to the output signal 148 of FIG. 7B, such as the baseline signal 168, the pulse height 166 and the time intervals 167a and 167b. In addition, the pulse-to-pulse signal 220 may be characterized by successive signal pulses 224a and 224b generated by the single particle 162 passing through the first and second light beams 194 and 196. The time-of-flight may be determined by establishing a time difference 226 between certain characteristics of the successive signal pulses 224a and 224b—e.g., the time difference between the respective peaks (as depicted), respective rising and/or falling edges, or other characteristics of the generated signals. It is noted that while the successive signal pulses 224a and 224b are depicted in FIG. 8D as having substantially the same pulse height 166 and pulse widths, the pulses 224a and 224b may have height and width characteristics that differ from each other without adverse effect.

Likewise, the pulse-to-pulse signal 222 is representative of a measurement made of a high concentration aerosol, and may have characteristics similar to the output signal 150 of FIG. 7C, such as the nominal offset value 170 and the time-averaged integrated level 172. The pulse-to-pulse signal 222, like signal 220, may be characterized by successive signal pulses 224a and 224b generated by the single particle 162 passing through the first and second light beams 194 and 196.

In operation, the integrated conditioner and pulse height conditioner circuits 100 and 104 may resolve the time-averaged integrated level 172 and the pulse height 166, respectively, to output the integrated outputs 102 and the pulse height outputs 106 to the digital processor 114 for determination of the mass concentration of the flow stream and the optical size of the distinctive particle 162, as previously described. Aerodynamic sizing may be inferred from the time difference 226. The inference of aerodynamic size may comprise use of a pulse-to-pulse calibration curve, such as by look-up tables or curve fit functions that are programmed into the digital processor 114. (See FIG. 12 and attendant discussion for an example of an aerodynamic sizing calibration curve using pulse-to-pulse data.)

Figure 9:
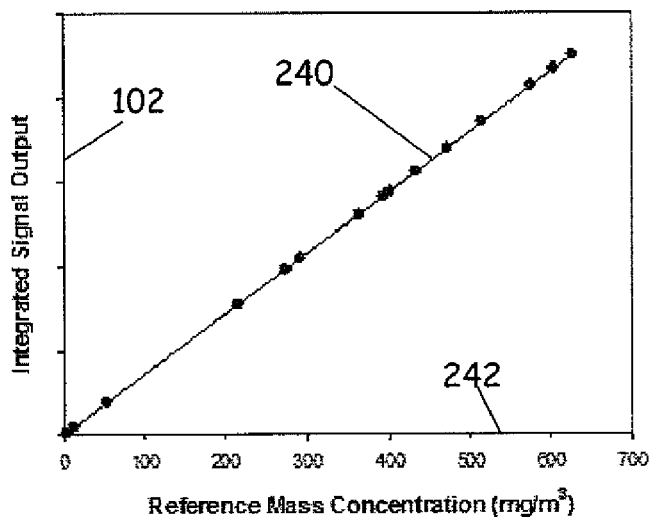
FIG. 9 depicts an integrated signal output as a function of particle mass concentration in an embodiment of the invention.

Referring to FIG. 9, a mass concentration calibration curve 240 plotting the integrated outputs 102 as a function of reference mass concentration 242 is depicted in an embodiment of the invention. For optically thin media, the integrated outputs 102 may be substantially linear with respect to the mass of the particles in the interrogation volume 50. Accordingly, the mass concentration calibration curve 240 may be established using a calibration aerosol from which a mass concentration of a test or field aerosol can be inferred using the integrated outputs 102. The accuracy of the calculated mass is generally affected by the differences between the size distribution, refractive index and the density of the particles within the test or field aerosol and those of the calibration aerosol. Also, the integrated outputs 102 may be relatively insensitive to particles larger than about 4 μm.

Figure 10:
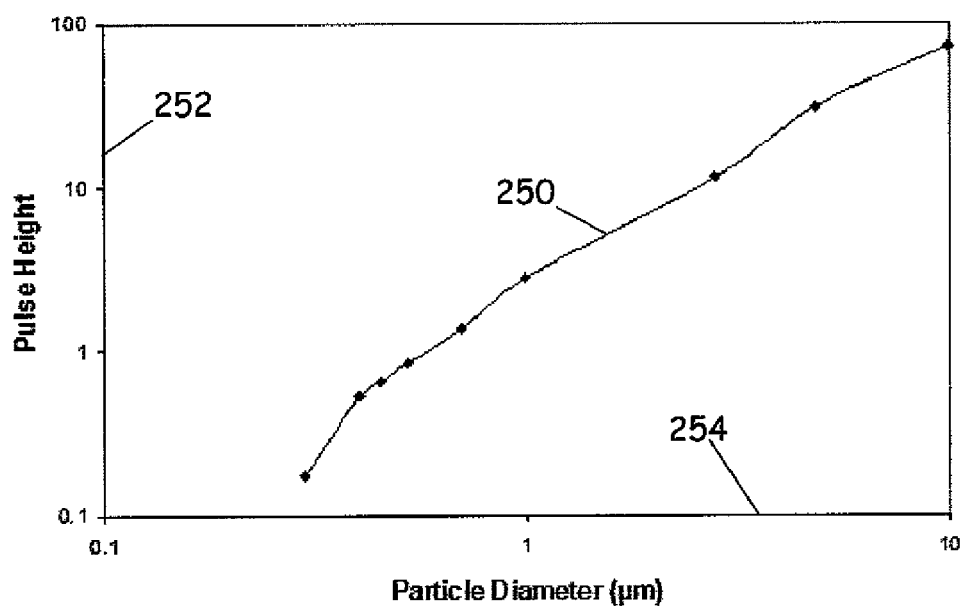
FIG. 10 is a logarithmic plot of the height of pulses generated by scattered light as a function of particle size in an embodiment of the invention.

Referring to FIG. 10, an example of the pulse height signal calibration curve 250 is presented in an embodiment of the invention. The pulse height signal calibration curve 250 presents a pulse height ordinate 252 as a function of a particle diameter abscissa 254. The pulse height signal calibration curve 250 in FIG. 10 was generated using polystyrene latex (PSL) particles of known particle diameters.

In operation, the pulse height signal calibration curve 250 may be programmed into the digital processor 114, such as by an empirical correlation (e.g., polynomial) or lookup table. The digital processor 114 receives the pulse height outputs 106 from the pulse height conditioner circuit 104, discerns a representative value of the pulse height (e.g., pulse height 176b) and converts the pulse height outputs 106 to a corresponding particle diameter. Discernment of the pulse height (e.g., 176b) may be taken as the difference between a maximum or peak value (e.g., 178b) and a nominal offset signal (e.g., 170) taken at the time of the rising edge of the pulse (see FIG. 4B and attendant discussion). The offset signal may be measured in real time.

Figure 11:
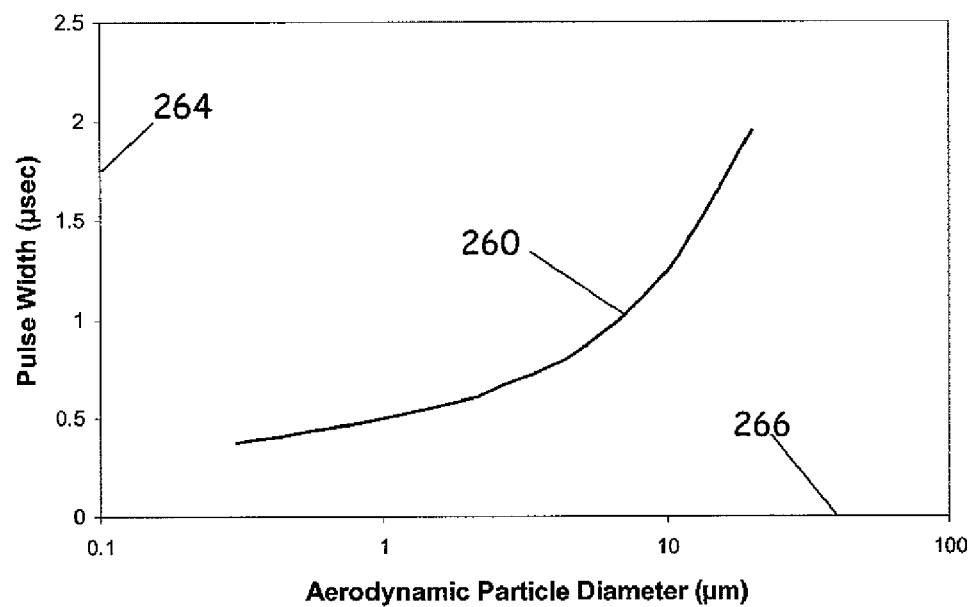
FIG. 11 is a semi-logarithmic plot of measured pulse width as a function of aerodynamic particle diameter in an embodiment of the invention.
Figure 12:
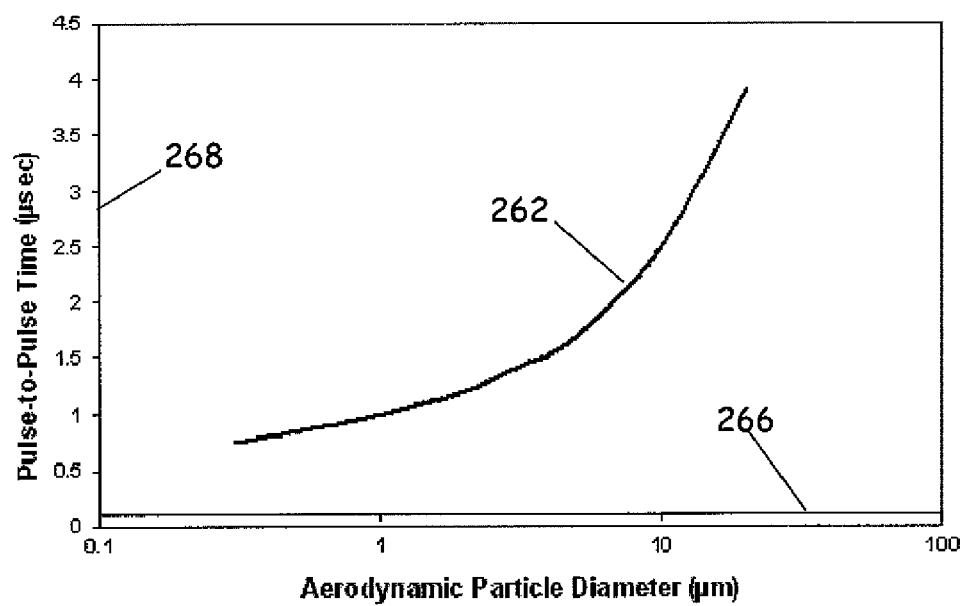
FIG. 12 is a semi-logarithmic plot of the time-of-flight of particles as a function of aerodynamic particle size for a dual-beam configuration in an embodiment of the invention.

Referring to FIGS. 11 and 12, sample aerodynamic particle diameter calibration curves 260 and 262 for use with the single beam and the dual beam time-of-flight techniques, respectively, are depicted. The single beam (pulse width) calibration 260 presents a pulse width 264 as a function of an aerodynamic particle diameter 266. The dual beam (pulse-to-pulse) calibration 262 presents a pulse-to-pulse time 268 as a function of the aerodynamic particle diameter 266.

Because larger particles may tend to be accelerated to a lesser extent by an increase in the flow rate of the aerosol, larger particles tend to traverse the light beam(s) at a slower rate of speed than smaller particles, as evinced by the longer durations of the pulse width (FIG. 11) or the pulse-to-pulse measurements (FIG. 12) at the larger aerodynamic particle diameters.

In operation, aerodynamic particle diameter calibrations 260 and 262 may be utilized to infer the particle aerodynamic diameter. One or both of the aerodynamic particle diameter calibration curves 260 and 262 may be programmed into the digital processor 114, such as by an empirical correlation (e.g., polynomial) or lookup table. The digital processor 114 receives the time-of-flight output 110 from the pulse height conditioner circuit 108, discerns a representative value of the time-of-flight (e.g., pulse width 164 or time difference 226) and converts the time-of-flight value to a corresponding aerodynamic particle diameter.

In some embodiments, an OPC technique may be utilized to infer a volume equivalent diameter ($d_e$) of a particle. The intensity of scattered light is a complex function of particle size, shape and refractive index. Typically, the OPC technique involves the calibration of a sensing device using particles having known physical properties, such as the PSL spheres or other spherical particles of known refractive index. By counting or binning the number of pulses related to a given particle size range, the particle number size distribution may be estimated, from which particle mass concentrations can be determined by calculating the mass of each particle or particle range.

Methods for calculating particle mass from the inferred particle size are presented below. Any mass concentrations derived directly from these particle mass calculations are hereinafter referred to as "size resolved" mass concentrations.

When the OPC technique is used, the pulse height produced by the test or field aerosols is compared to the pulse height signal calibration curve to obtain the optical equivalent diameter ($d_o$), which is defined as the particle diameter of the test or field aerosol that scatters the same amount of light as the calibration aerosol. Assuming particles are spherical, and $d_o = d_e$, an optical particle mass $m_o$ can be inferred as follows:

$$m_O = \frac{\pi}{6}\rho_p d_e^3 = \frac{\pi}{6}\rho_p d_o^3, \qquad \text{Eqn. (1)}$$

where $\rho_p$ is the particle density. Note that the mass estimation is proportional to $\rho_p$. Also, it is known that the difference between $d_o$ and $d_e$ is a function of the shape and refractive index of the particle. See Willeke et al., *Fine Particles: Aerosol Generation, Measurement, Sampling, and Analysis*, pp. 698-729, 1976.

Uncertainties created by these factors may be reduced if the pulse height signal calibration curve is obtained using aerosols of interest. Alternatively, if the refractive index of the test particle is known, the scattering response difference between the test and calibration aerosols can be corrected using the theoretical scattering response calculation as described by Bohren C. F. and Huffman D. R. "Absorption and scattering of light by small particles," Willey Science Paperback Series, 1998, which is hereby incorporated by reference herein other than express definitions of terms specifically defined therein.

An APS technique may also be utilized in place of or in addition to the OPC technique to infer a volume equivalent diameter ($d_e$) of a particle. One APS technique is formulated as follows:

$$m_A = \frac{\pi}{6}\rho_p d_e^3 = \frac{\pi}{6}\rho_0 d_a^3 \left(\frac{\rho_0}{\rho_p}\right)^{\frac{1}{2}} \chi^{\frac{3}{2}}, \qquad \text{Eqn. (2)}$$

where $m_A$ is the aerodynamic particle mass, $\rho_0$ is the unit density (1 g/cm$^3$) and $\chi$ is a dynamic shape factor which accounts for the influence of the shape of the particle on the motion of the particle.

The determination of the aerodynamic particle mass according to Eqn. (2) is proportional to $\rho_p$ $$-\frac{1}{2}.$$

Moreover, the dynamic shape factor $\chi$ is often close to unity, ranging typically from 1.0 to 1.2; hence, the sensitivity of the mass determination MA to the dynamic shape factor $\chi$ of Eqn. (2) is often secondary relative to other parameters such as density and refractive index. Therefore, the APS technique of Eqn. (2) may, in some instances, provide a more accurate estimate of particle mass than does the OPC technique of Eqn. (1).

There are instances, however, where the OPC technique of Eqn. (1) may provide accuracy superior to the APS technique of Eqn. (2). At the smaller aerodynamic particle diameters, the aerodynamic particle diameter calibration curves of FIGS. 11 and 12 flatten out, indicating a reduction in the size resolution using the APS technique. The pulse height signal calibration curve of FIG. 10, on the other hand, retains a sensitivity that is fairly consistent across the range of the calibration. Thus, there may be applications where the OPC technique of Eqn. (1) is better than the APS technique of Eqn. (2) for the characterization of smaller diameter particles. Accordingly, the size segregated mass concentration measurement system 30 may be configured to so that the aerodynamic particle size is utilized to characterize a first size range of particles and the optical particle size is utilized to characterize second size range of particles, with the first size range having an average value that is greater than a average value of the second size range. Generally, the APS technique may be preferable for particle diameters above approximately 2.5-μm and the OPC technique for particle diameters less than approximately 1.0- to 2.5-μm for calculating aerosol mass concentration.

The integrated signal may be insensitive to particles that are larger than the wavelength of light source. Accordingly, it may be presumed that the integrated signal is representative of finer particulate mass such as PM2.5 or respirable aerosol. For example, assuming the integrated signal is calibrated to represent PM2.5, the PM1 and PM10 size fractions may be determined by $$PM1 = PM2.5 - PM1\text{-}2.5, \qquad \text{Eqn. (3)}$$

$$PM10 = PM2.5 + PM2.5\text{-}10, \qquad \text{Eqn. (4)}$$

where PM1-2.5 and PM2.5-10 are the mass concentration in the size range of 1- to 2.5-μm and 2.5- to 10-μm, respectively. They are determined by single particle measurement using the OPC and/or APS techniques.

Functionally, the scheme presented for processing of a high concentration particle stream is valid for aerosol flow streams where the concentrations of larger particles (e.g., particles with diameters greater than 1 μm) are always low enough (e.g., less than 15% coincidence error) to preclude an unacceptable occurrence rate of coincidence, even though small particles signals are not distinguishable due to coincidence.

The total or integrated signal depends generally on certain characteristics of the aerosol such as particle size distribution, particle refractive index, particle shape. That is, aerosols with the same mass concentrations but different characteristics will generate different integrated signals. Because the integrated signal is calibrated with aerosols having certain characteristics, the integrated measurement may be inaccurate when the test aerosol is different from that of the calibration aerosol.

The accuracy of the size segregated mass output of the instrument may be improved by manually entering the information about the aerosol encountered in the field or by calibration with the actual aerosols encountered in the field. A library of calibration factors which account for the shape, refractive index and density of different aerosols commonly encountered in the environment or workplace can be programmed into the instrument so that the user can pick a field aerosol type (calibration factor) directly from the library that is applicable to a given application. The accuracy of the instrument can also be improved by using field calibration techniques described below.

In various embodiments, a photometric calibration factor CFp can be experimentally determined to correct the integrated signal for a more accurate determination of fine particle mass concentration. For example, if the integrated signal is to be calibrated to represent the PM2.5 mass fraction, one can install an inlet conditioner (e.g., PM2.5 impactor) at the inlet of a gravimetric sampling device and sample the aerosol of interest simultaneously with an embodiment of the present invention. The photometric calibration factor CFp is calculated as the ratio of PM2.5 mass concentration measured by the gravimetric sampling device and to the PM2.5 mass concentration measured by the instrument.

An aerosol inlet conditioner such as 2.5 μm cut impactor can be used to improve the size segregated mass measurement accuracy of the coarser fraction of aerosol of unknown characteristics. For example, assume that the instrument was calibrated in the factory using Arizona road dust. The calibration aerosol can be sampled by the instrument without the inlet conditioner in place and with the inlet conditioner in place. These two samples can be compared and the 50% cut off point of the inlet conditioner can be determined. In factory the calibration factors are set such that the 50% cut off point ($D_{50c}$) of a 2.5 μm inlet conditioner is 2.5 μm. The field aerosol of unknown characteristics can be sampled without the inlet conditioner in place and with the inlet conditioner in place. From these two measurements, the 50% cut off point for the field ($D_{50f}$) aerosol can be determined by the instrument. A size calibration factor CFs can be calculated as follows:

$$CFs = D_{50c}/D_{50f} \qquad \text{Eqn. (5)}$$

In another embodiment, the inlet conditioner may be used in conjunction with a gravimetric sampling filter arranged to capture the conditioned aerosol or a representative portion thereof after it passes through the optics chamber. A customer calibration factor can be created with the precut test aerosol by comparing the results of the size segregated mass concentration measurement system with the gravimetric filter results.

Another way to improve measurement accuracy is to fit the size distribution to certain representative distributions, such as the lognormal distributions commonly found in atmospheric aerosols. By knowing the expected profile of the size distribution, one can identify outliers in the distribution that may occur because of noise or other anomalies that occurred in the measurement and conversion process. The fitted size distribution may be converted to mass distribution, often with improved accuracy.

In some embodiments of the invention, the test aerosol size distribution may be measured in real time by the APS and/or OPC techniques, which can be compared to that of the calibration aerosol. A correction factor can be generated to correct the integrated signal for a more accurate determination of mass concentration. To give an example, assume an integrated signal calibration $R_{cal}$ per unit mass response to a calibration aerosol. If the result of the APS and/or OPC technique indicates that the test aerosol has a different size distribution than the calibration aerosol, the integrated signal response per unit mass to this aerosol, $R_{test}$, may be different from the calibration response $R_{cal}$. The value of $R_{test}$ is determined from calibration. The true mass concentration ($M_{true}$) after correcting the instrument indicated mass concentration ($M_{indicate}$) for the size difference is then $$M_{true} = M_{indicate} \times \frac{R_{cal}}{R_{test}}. \qquad \text{Eqn. (5)}$$

The aerosol flow rate (FIG. 1) determines the cut size of the precut devices such as an impactor or cyclone, and is also used to calculate particle concentrations in the single particle counting mode and the gravimetric filter sampling. There are many different ways to measure or control the flow rates. The flowmeter may be a device that measures the pressure drop across flow restriction such as an orifice, nozzle or a venturi. The flow could also be measured by measuring a heat loss from a heated element, a positive displacement device such as a turbine flow meter, or other appropriate flow measurement techniques known to the artisan.

Consider a volumetric aerosol flow rate at the inlet of $Q_1$, an exhaust flow rate is $Q_2$, and a sheath/curtain air flowrate is $Q_3$. Also presume a temperature and pressure of the gas is $T_1$, $P_1$ at the inlet and $T_2$, $P_2$ at the flowmeter. The pump can be controlled so that the inlet and exhaust have the same mass flow rates. That is, $$Q_1 \frac{P_1}{T_1} = Q_2 \frac{P_2}{T_2} \qquad \text{Eqn. (6)}$$

The sheath/curtain flow rate can be controlled by adjusting the orifice diameter in the sheath air line when it is recirculated.

It is noted that while the above discussion makes frequent reference to "light" as the propagated, scattered and collected medium, such use is not to be construed as limiting the invention to application in the visible portion of the electromagnetic spectrum. Rather, various embodiments of the invention may encompass any portion of the electromagnetic spectrum appropriate for a given application, including but not limited to the ultraviolet, visible, and infrared portions of the electromagnetic spectrum, collimated or uncollimated.

The embodiments above are intended to be illustrative and not limiting. Although aspects of the present invention have been described with reference to particular embodiments, those skilled in the art will recognize that changes can be made in form and detail without departing from the spirit and scope of the invention. Any incorporation by reference of or other reference to documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. An instrument for measuring size segregated mass concentration of an aerosol, comprising:
   an electromagnetic radiation source operatively coupled with beam shaping optics for generation of a beam of electromagnetic radiation;

an inlet nozzle for passage of an aerosol flow stream therethrough, said aerosol flow stream containing particles and intersecting said beam of electromagnetic radiation to define an interrogation volume, said particles scattering said electromagnetic radiation from said interrogation volume;

a radiation collector for collection of a portion of said electromagnetic radiation scattered from said interrogation volume;

a detector for detection of said portion of said electromagnetic radiation collected by said radiation collector;

a plurality of signal conditioners including an integrated signal conditioner and at least one of a pulse height signal conditioner and a time-of-flight signal conditioner, each of said plurality of signal conditioners being operatively coupled to said detector and each generating a respective output;

a digital processor operatively coupled with said plurality of signal conditioners for conversion of each of said respective outputs to a mass concentration and to at least one of an optical particle size and an aerodynamic particle size.

2. The instrument of claim 1 further comprising:

additional beam shaping optics for generation of a second beam of electromagnetic radiation, said second beam of electromagnetic radiation intersecting said aerosol flow stream to define a second interrogation volume, said particles scattering said electromagnetic radiation from said second interrogation volume, said radiation collector being arranged for collection of a portion of said electromagnetic radiation scattered from said second interrogation volume, and wherein said plurality of signal conditioners includes said time-of-flight signal conditioner.

3. The instrument of claim 1 wherein said additional beam shaping optics comprises a beam splitter and said second beam of electromagnetic radiation is sourced by said electromagnetic radiation source.

4. The instrument of claim 1 wherein said inlet nozzle is an accelerating inlet nozzle.

5. The instrument of claim 1 further comprising a gravimetric filter positioned downstream of said interrogation volume.

6. A method for determining size segregated aerosol mass concentration, comprising:

providing a detector operatively coupled with an integrated signal conditioner and with a pulse height signal conditioner, said detector configured to receive electromagnetic radiation scattered from an interrogation volume;

causing particles to flow through said interrogation volume and scatter electromagnetic radiation onto said detector to generate an electrical signal from said detector;

generating an integrated output from said electrical signal with said integrated signal conditioner, said integrated output being proportional to a mass of particles flowing through said interrogation volume during a predetermined time interval;

generating a plurality of pulse height outputs from said electrical signal with said pulse height signal conditioner, each of said pulse height outputs corresponding to a particle passing through said interrogation volume and corresponding to an optical particle size greater than a predetermined value; and determining a size segregated mass concentration from said from said integrated output and said plurality of pulse height outputs.

7. The method of claim 6, further comprising:

inferring a plurality of optical particle sizes from said plurality of pulse height outputs and said integrated output, one for each of said plurality of pulse height outputs;

calculating a plurality of optical particle masses from said plurality of optical particle sizes, one optical particle mass for each of said plurality of optical particle sizes;

inferring a mass concentration from said integrated output; and determining a size segregated mass concentration from said mass concentration and said plurality of optical particle masses.

8. The method of claim 6 wherein said step of providing said detector further comprises providing said detector operatively coupled with a time-of-flight signal conditioner.

9. The method of claim 8 further comprising:

generating a plurality of time-of-flight outputs from said electrical signal with said time-of-flight signal conditioner, each of said time-of-flight outputs corresponding to a particle passing through said interrogation volume and corresponding to an aerodynamic particle size greater than a predetermined value;

inferring a plurality of aerodynamic particle sizes from said plurality of time-of-flight outputs and said integrated output, one for each of said plurality of time-of-flight outputs;

calculating a plurality of aerodynamic particle masses from said plurality of aerodynamic particle sizes, one aerodynamic particle mass for each of said plurality of aerodynamic particle sizes;

inferring a mass concentration from said integrated output; and determining a size segregated mass concentration from said from said mass concentration and said plurality of aerodynamic particle masses.

10. The method of claim 9 wherein said step of generating said time-of-flight value further comprises resolving a pulse width and inferring said time-of-flight value from said pulse width.

11. The method of 9 wherein said aerodynamic particle size is utilized to characterize a first size range of particles and said optical particle size is utilized to characterize second size range of particles, said first size range having a first average value, said second size range having a second average value, said first average value being greater than said second average value.

12. The method of claim 11 wherein said first size range includes particles greater than approximately 1 micrometer.

13. The method of claim 11 wherein said second size range includes particles less than approximately 2.5 micrometers.

14. A method for determining size segregated aerosol mass concentration, comprising:

providing a detector operatively coupled with an integrated signal conditioner and with a time-of-flight signal conditioner, said detector configured to receive electromagnetic radiation scattered from an interrogation volume;

causing particles to flow through said interrogation volume and scatter electromagnetic radiation onto said detector to generate an electrical signal from said detector;

generating an integrated output from said electrical signal with said integrated signal conditioner, said integrated output value being proportional to a mass of particles flowing through said interrogation volume during a predetermined time interval;

generating a plurality of time-of-flight outputs from said electrical signal with said time-of-flight signal conditioner, each of said time-of-flight outputs corresponding to a particle passing through said interrogation volume and corresponding to an aerodynamic particle size greater than a predetermined value; and determining a size segregated mass concentration from said from said integrated output and said plurality time-of-flight outputs.

15. The method of claim 14 wherein said step of generating said time-of-flight value further comprises resolving a pulse width and inferring said time-of-flight value from said pulse width.

16. The method of claim 14, further comprising:
inferring a mass concentration from said integrated output;
inferring a plurality of aerodynamic particle sizes from said plurality of time-of-flight outputs and said integrated output, one aerodynamic particle size for each of said plurality of time of flight outputs;
calculating a plurality of aerodynamic particle masses from said plurality of aerodynamic particle sizes, one aerodynamic particle mass for each of said plurality of aerodynamic particle sizes; and
determining a size segregated mass concentration from said from said mass concentration and said plurality of aerodynamic particle masses.

17. The method of claim 14 wherein said step of providing said detector further comprises providing said detector operatively coupled with a pulse height signal conditioner.

18. The method of claim 17 further comprising:
generating a plurality of pulse height outputs from said electrical signal with said pulse height signal conditioner, each of said pulse height outputs corresponding to a particle passing through said interrogation volume and corresponding to an optical particle size greater than a predetermined value;
inferring a plurality of optical particle sizes from said plurality of pulse height outputs and said integrated output, one for each of said plurality of pulse height outputs;
calculating a plurality of optical particle masses from said plurality of optical particle sizes, one optical particle mass for each of said plurality of optical particle sizes;
inferring a mass concentration from said integrated output; and
determining a size segregated mass concentration from said from said mass concentration and said plurality of optical particle masses.

19. The method of 18 wherein said aerodynamic particle size is utilized to characterize a first size range of particles and said optical particle size is utilized to characterize second size range of particles, said first size range having a first average value, said second size range having a second average value, said first average value being greater than said second average value.

20. The method of 19 wherein said first size range includes particles greater than approximately 1 micrometer.

21. The method of 19 wherein said second size range includes particles less than approximately 2.5 micrometers.

22. A device for determining size segregated aerosol mass concentration, comprising:
a detector operatively coupled to an integrated signal conditioner and at least one of a pulse height signal conditioner and a time-of-flight signal conditioner, said integrated signal conditioner for generation of an integrated output, said pulse height signal conditioner for generation of a pulse height output, said time-of-flight signal conditioner for generation of a time-of-flight output;
a signal processor configured to receive said integrated signal output and at least one of said pulse height output and said time-of-flight signal output, said signal processor including a microprocessor and a storage device, said storage device including instructions executable by said microprocessor, said instructions including:
resolving an integrated mass concentration from said integrated output; and
resolving a particle size from at least one of said pulse height output and said time-of-flight output.

23. The device of claim 22 wherein said instructions executable by said microprocessor further include:
using said particle size to calculate a size resolved mass concentration;
inferring a size segregated mass concentration from said integrated mass concentration and said size resolved mass concentration, said size segregated mass concentration having a plurality of size fraction bands.

24. The device of claim 23 wherein said size fraction bands include one or more of a PM1, a PM2.5, a respirable fraction and a PM10.

25. The device of 23 wherein said detector is operatively coupled to said pulse height signal conditioner and said time-of-flight signal conditioner, and wherein said instructions executable by said microprocessor further includes:
determining particle size for particles within a first size range using said pulse height output;
determining particle size for particles within a second size range using said time-of-flight output, said second size range having an average size that is greater than an average size of said first size range; and
determining a size resolved mass concentration from said first and second size ranges.

26. The device of claim 25 wherein said second size range is greater than about 1 micrometer.

27. The device of claim 25 wherein said first size range is less than about 2.5 micrometers.

28. A method for determining size segregated aerosol mass concentration, comprising:
providing a detector operatively coupled with a pulse height signal conditioner and a time-of-flight signal conditioner, said pulse height signal conditioner for generation of a pulse height output, said time-of-flight signal conditioner for generation of a time-of-flight output;
causing said detector to receive electromagnetic radiation scattered from a particle;
resolving an optical particle size value from said pulse height output;
resolving an aerodynamic particle size from said time-of-flight output;
establishing a size of said particle to be said optical particle size if one of said optical particle size and said aerodynamic particle size is less than a predetermined value; and
establishing a size of said particle to be said aerodynamic particle size if one of said optical particle size and said aerodynamic particle size is greater than a predetermined value.

29. The method of claim 28 wherein said predetermined value is about 2.5 micrometers.

* * * * *

UNITED STATES PATENT AND TRADEMARK OFFICE
CERTIFICATE OF CORRECTION

PATENT NO. : 7,932,490 B2
APPLICATION NO. : 12/187827
DATED : April 26, 2011
INVENTOR(S) : Xiaoliang Wang et al.

It is certified that error appears in the above-identified patent and that said Letters Patent is hereby corrected as shown below:

On the Title Page:

Other Publications, Page 2, Col. 2 reference 3. Delete "January 1, 2006, 3549", insert -- 2006-01-3494 --

In the Specifications:

Col. 12, line 53, delete "23 and 2c", and insert -- 2B and 2C --

Col. 13, line 36, delete "of by the radiation", insert -- by the radiation --

Col. 16, line 54, delete "FW technique", insert -- FWHM technique --

Col. 16, line 49, delete "FIGS. 5A and", insert -- FIGS. 8A --

Col. 19, line 15, delete "5B", insert -- 8B --

Col. 21, lines 58-62, delete "pp    -1/2.", insert -- $p_a^{-1/2}$ --

Col. 21, line 66, delete "determination MA to the", insert -- determination $m_A$ to the --

In the Claims:

Col. 25, claim 6, lines 65-66, delete "from said from said", insert -- from said --

Col. 26, claim 9, lines 33-34, delete "from said from said", insert -- from said --

Col. 27, claim 14, lines 4-5, delete "from said from said", insert -- from said --

Col. 27, claim 16, lines 22-23, delete "from said from said", insert -- from said --

Col. 27, claim 18, lines 43-44, delete "from said from said", insert -- from said --

Signed and Sealed this
Twenty-third Day of April, 2013

Teresa Stanek Rea
*Acting Director of the United States Patent and Trademark Office*